US010893845B2

(12) United States Patent
Asai

(10) Patent No.: US 10,893,845 B2
(45) Date of Patent: *Jan. 19, 2021

(54) WHEEZING DETECTION APPARATUS

(71) Applicant: OMRON HEALTHCARE CO., LTD., Muko (JP)

(72) Inventor: Kei Asai, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 391 days.

This patent is subject to a terminal disclaimer.

(21) Appl. No.: 15/669,642

(22) Filed: Aug. 4, 2017

(65) Prior Publication Data

US 2017/0325777 A1    Nov. 16, 2017

Related U.S. Application Data

(63) Continuation of application No. PCT/JP2015/082503, filed on Nov. 19, 2015.

(30) Foreign Application Priority Data

Feb. 27, 2015 (JP) .................................. 2015-039257

(51) Int. Cl.
| | | |
|---|---|---|
| *A61B 5/08* | (2006.01) | |
| *A61B 7/00* | (2006.01) | |
| *A61B 7/04* | (2006.01) | |
| *A61B 5/00* | (2006.01) | |

(52) U.S. Cl.
CPC ............ *A61B 7/003* (2013.01); *A61B 5/0803* (2013.01); *A61B 5/0816* (2013.01);
(Continued)

(58) Field of Classification Search
CPC ......... A61B 7/003; A61B 7/04; A61B 5/0803; A61B 5/0816; A61B 5/6833;
(Continued)

(56) References Cited

U.S. PATENT DOCUMENTS

| | | | |
|---|---|---|---|
| 6,168,568 B1 * | 1/2001 | Gavriely | ................ A61B 5/087 600/529 |
| 2007/0118054 A1 * | 5/2007 | Pinhas | ................. A61B 5/1104 600/587 |

(Continued)

FOREIGN PATENT DOCUMENTS

| | | | |
|---|---|---|---|
| JP | 2001-505085 A | 4/2001 | |
| JP | 2005000388 A * | 1/2005 | ............... A61B 5/11 |
| JP | 2013-521833 A | 6/2013 | |
| JP | 2014-050614 A | 3/2014 | |

OTHER PUBLICATIONS

The English-language machine translation of JP2005000388A (Year: 2019).*

(Continued)

*Primary Examiner* — Navin Natnithithadha
*Assistant Examiner* — Andrey Shostak
(74) *Attorney, Agent, or Firm* — Oliff PLC

(57) ABSTRACT

A wheezing detection apparatus includes a breathing sound detection unit that detects a breathing sound of a measurement subject and acquires a breathing sound signal in a time series expressing the breathing sound. The wheezing detection apparatus includes a determination processing unit that, in each pre-determined processing unit period, converts the breathing sound signal into a frequency space to acquire a frequency spectrum of the breathing sound, and based on a height and a width of a peak in the frequency spectrum, determines whether or not the peak indicates wheezing.

7 Claims, 21 Drawing Sheets

(52) U.S. Cl.
CPC .......... *A61B 5/6833* (2013.01); *A61B 5/7275* (2013.01); *A61B 5/7282* (2013.01); *A61B 5/742* (2013.01); *A61B 7/04* (2013.01); *A61B 5/08* (2013.01); *A61B 2503/04* (2013.01)

(58) Field of Classification Search
CPC ..... A61B 5/7275; A61B 5/742; A61B 5/7282; A61B 5/08; A61B 2503/04
See application file for complete search history.

(56) References Cited

U.S. PATENT DOCUMENTS

| | | | |
|---|---|---|---|
| 2008/0306367 A1* | 12/2008 | Koehler | A61B 5/4255 600/364 |
| 2011/0076349 A1* | 3/2011 | Yoshihara | A61K 36/896 424/774 |
| 2011/0125044 A1 | 5/2011 | Rhee et al. | |
| 2011/0230777 A1* | 9/2011 | Fu | A61B 7/003 600/529 |
| 2013/0102908 A1* | 4/2013 | Ser | A61B 7/003 600/484 |
| 2013/0303892 A1* | 11/2013 | Zhao | A61B 5/061 600/424 |

OTHER PUBLICATIONS

Feb. 16, 2016 Search Report issued in International Patent Application No. PCT/JP2015/082503.

\* cited by examiner

WHEEZING DETECTION APPARATUS

TECHNICAL FIELD

The present invention relates to a wheezing detection apparatus, and more specifically relates to a wheezing detection apparatus that detects whether or not wheezing is included in a breathing sound of a measurement subject.

BACKGROUND ART

For example, Patent Document 1 (US 2011/0125044 A1) discloses an automated system for observing a respiratory disease such as asthma. The system provides a summary of data and a warning when the severity of symptoms reaches a threshold value based on data from a microphone and an accelerometer. In particular, for wheezing, peaks of a frequency spectrum in a frequency range of about 200 to 800 Hz is measured, the peaks of the frequency spectrum and a predetermined value that is associated with wheezing and is stored in the memory are compared, and the result of the comparison is used as an element for determining the severity.

CITATION LIST

Patent Literature

Patent Document 1: US 2011/0125044 A1

SUMMARY OF INVENTION

Technical Problem

However, with the above-described system, since only the magnitudes of the peaks of the frequency spectrum and the reference value (value stored in the memory) are compared for wheezing, there is a problem in that the accuracy of detecting wheezing is not good.

In view of this, the present invention aims to provide a wheezing detection apparatus that can accurately detect whether or not wheezing is included in a breathing sound of a measurement subject.

Solution to the Problem

In order to solve the above-described problem, the wheezing detection apparatus of the present invention includes:

a breathing sound detection unit configured to detect a breathing sound of a measurement subject and acquire a breathing sound signal in a time series expressing the breathing sound; and a determination processing unit configured to, in each pre-determined processing unit period, convert the breathing sound signal into a frequency space to acquire a frequency spectrum of the breathing sound, and determine whether or not a peak in the frequency spectrum indicates wheezing based on a height and a width of the peak.

Here, the above-described "peaks" in the frequency spectrum refers to peaks of sound intensity (sound pressure). The "height" and "width" of a peak in the frequency spectrum refer to the "height" and "width" of a peak in a graph of frequency with respect to sound pressure. Also, if background noise exists in the graph of frequency with respect to sound pressure, the "height" and "width" refer to the substantial "height" and "width" of the peak from which the background noise has been removed.

In the analysis performed by the inventor, a whistle-like sound of wheezing is characterized in that the widths of peaks in its frequency spectrum are relatively narrow (close to being monotone). Also, a wheezing sound is characterized in that it includes several peaks with relatively narrow widths. Accordingly, in order to accurately detect wheezing, the widths of the peaks in the frequency spectrum should be incorporated in the determination in some way. Here, in the wheezing detection apparatus of the present invention, the breathing sound detection unit detects the breathing sound of the measurement subject and acquires the breathing sound signal in a time series expressing the breathing sound. In each predetermined processing unit period, the determination processing unit converts the breathing sound signal into a frequency space to acquire a frequency spectrum of the breathing sound, and based on the heights and widths of the peaks in the frequency spectrum, determines whether or not the peaks indicate wheezing. As a result, it is possible to accurately detect whether or not wheezing is included in the breathing sound of the measurement subject.

With the wheezing detection apparatus according to an embodiment, the determination processing unit obtains a ratio between the height and the width of the peak and determines whether or not the wheezing is indicated based on whether or not the ratio is greater than a pre-determined first threshold value.

With the wheezing detection apparatus according to the embodiment, the determination processing unit obtains a ratio between the height and the width of the peak and determines whether or not the wheezing is indicated based on whether or not the ratio is greater than a pre-determined first threshold value. As a result, it is possible to more accurately detect whether or not wheezing is included in the breathing sound of the measurement subject.

With the wheezing detection apparatus according to an embodiment, the determination processing unit determines whether or not the wheezing is indicated based on only a dominant peak having the largest area among a plurality of peaks in the frequency spectrum in a graph of frequency with respect to sound pressure.

In view of this, the "area" on the graph of frequency with respect to sound pressure means the substantial area from which background noise has been removed.

A dominant peak that has the largest area in the graph of frequency with respect to sound pressure among the multiple peaks in the frequency spectrum corresponds to the peak having the highest energy. Accordingly, the dominant peak determines whether or not wheezing is included in the above-described unit period for processing. In view of this, with the wheezing detection apparatus according to the embodiment, the determination processing unit determines whether or not the wheezing is indicated based on only a dominant peak having the largest area among a plurality of peaks in the frequency spectrum in a graph of frequency with respect to sound pressure. As a result, it is possible to more accurately detect whether or not wheezing is included in the breathing sound of the measurement subject.

With the wheezing detection apparatus according to an embodiment, the determination processing unit determines whether or not the wheezing is indicated based only on a peak with a frequency ranging from 200 Hz to 1500 Hz in the frequency spectrum.

In the analysis performed by the inventor, the whistle-like sound of wheezing that is often observed in cases of infantile asthma is a sound with peaks having widths that are relatively narrow (a sound that is close to monotone) in the frequency range of about 900 Hz to 1200 Hz. In view of this, with the wheezing detection apparatus according to the embodiment, the determination processing unit determines whether or not the wheezing is indicated based only on a peak with a frequency ranging from 200 Hz to 1500 Hz in the frequency spectrum. Accordingly, it is possible to detect whether or not wheezing including whistle-like wheezing that is often observed in the case of infantile asthma is included in the breathing sound of the measurement subject, in addition to the wheezing sound. On the other hand, sounds outside of the 200 Hz to 1500 Hz range are not thought of as being wheezing, and therefore are not handled in the determination. As a result, it is possible to more accurately detect whether or not wheezing is included in the breathing sound of the measurement subject.

A wheezing detection apparatus according to an embodiment includes: an addition processing unit configured to set an addition unit period including a plurality of the processing unit periods, add up the lengths of processing unit periods that were determined to include the wheezing in each addition unit period, and obtain the result as a wheezing period, wherein in each of the processing unit periods, the addition processing unit converts the breathing sound signal into a frequency space to acquire the frequency spectrum of the breathing sound, classifies the power of the wheezing sound into multiple levels based on the area of the dominant peak that has the largest area in the graph of frequency with respect to sound pressure among the plurality of peaks in the frequency spectrum, and adds up the lengths of the processing unit periods that were determined to include the wheezing in each of the classified levels; and a warning generation unit configured to generate a warning when a percentage of time for which a power of the wheezing sound reaches a specific level in the addition unit period exceeds a pre-determined second threshold value based on the addition performed by the addition processing unit.

Here, generation of a "warning" widely includes generation of an alarm sound, alarm display on a display screen, wireless alarm signal transmission, and the like.

With the wheezing detection apparatus according to the embodiment, the addition processing unit sets the unit addition period, which includes multiple processing unit periods, adds up the lengths of the processing unit periods in the addition unit period which were determined to include wheezing, and obtains the result as the wheezing period. In each of the processing unit periods, the addition processing unit converts the breathing sound signal into a frequency space to acquire the frequency spectrum of the breathing sound, classifies the power of the wheezing sound into multiple levels based on the area of the dominant peak that has the largest area in the graph of frequency with respect to sound pressure among the multiple peaks in the frequency spectrum, and adds up the lengths of the processing unit periods for which it was determined that the wheezing is included in each of the classified levels. When the percentage of time for which the power of the wheezing sound has reached a specific level exceeds a predetermined second threshold value in the addition unit period, the warning generation unit generates a warning. With this warning, the user (typically indicates the measurement subject, a guardian or caregiver who cares for the measurement subject, a medical professional such as a nurse, or the like) can be made aware of the fact that the symptoms of the measurement subject have worsened, and thus can take a countermeasure such as administering medication to the measurement subject. This warning is particularly advantageous in the case where the measurement subject is an infant, a seriously ill patient, or the like, who has difficulty expressing intention.

With the wheezing detection apparatus according to an embodiment, a sound recording unit configured to record the breathing sound signal when the warning generation unit generates the warning is included.

With the wheezing detection apparatus according to the embodiment, a sound recording unit records the breathing sound signal when the warning generation unit generates a warning. Accordingly, it is possible to automatically record the breathing sound of the measurement subject when the wheezing is relatively large (i.e., when the wheezing is severe). Accordingly, by replaying the recorded content the next time the measurement subject has a medical examination, for example, the user can have a doctor listen to the breathing sound of the measurement subject for when the wheezing is severe. As a result, it is easier for the doctor to diagnose whether or not the measurement subject has asthma and the severity of the asthma, and the doctor can easily create a treatment plan.

The wheezing detection apparatus of an embodiment furthermore includes:

a phase identification unit configured to identify the breathing cycle of the measurement subject by dividing it into an expiratory phase and an inspiratory phase, based on the breathing sound signal acquired by the breathing sound detection unit;

a phase instruction input unit configured to input an instruction to select one or both of the expiratory phase and the inspiratory phase of the breathing sound signal; and a sound recording unit configured to record the phase of the breathing sound signal instructed by the phase instruction input unit.

With the wheezing detection apparatus according to the embodiment, the phase identification unit identifies the breathing cycle of the measurement subject with a distinction made between the expiratory phase and the inspiratory phase, based on the breathing sound signal acquired by the breathing sound detection unit. In response to a request made by the doctor, for example, the user uses the phase instruction input unit to input an instruction to select one or both of the inspiratory phase and the expiratory phase in the breathing sound signal. Upon doing so, the sound recording unit records the phase of the breathing sound signal instructed by the phase instruction input unit. Accordingly, when the doctor listens to the recorded content of the wheezing during the next medical examination, the user can have the doctor listen to the recorded content of the phase of the breathing cycle requested by the doctor.

With the wheezing detection apparatus of an embodiment, the breathing sound detection unit includes:

a first microphone in the form of a stethoscope attached to skin of the chest of the measurement subject; and a second microphone attached to clothing or skin of a part located away from the chest and respiratory organ of the measurement subject, and the breathing sound detection unit outputs a difference obtained by subtracting the output of the second microphone from the output of the first microphone is output.

Here, the first microphone and the second microphone being "attached" includes a mode of being adhered via an adhesive sheet, for example. The "clothing" to which the second microphone is attached indicates clothing such as underclothes, for example. The "part located away from the chest and the respiratory organs" to which the second microphone is attached indicates a part such as a shoulder, for example, at which the breathing sound has little influence.

With the wheezing detection apparatus of the embodiment, the breathing sound detection unit includes a first microphone in the form of a stethoscope attached to the skin of the chest of the measurement subject, and a second microphone attached to clothing or the skin of a part located away from the chest and the respiratory organ of the measurement subject. Also, a difference obtained by subtracting the output of the second microphone from the output of the first microphone is output. Accordingly, noise components in the surroundings of the measurement subject can be removed from the breathing sound signal. As a result, it is possible to more accurately detect whether or not wheezing is included in the breathing sound of the measurement subject.

Advantageous Effects of the Invention

As is evident from the description above, with the wheezing detection apparatus of the present invention, it is possible to accurately detect whether or not wheezing is included in the breathing sound of the measurement subject.

DESCRIPTION OF EMBODIMENTS

Hereinafter, embodiments of the present invention will be described in detail with reference to the drawings.

Figure 1:
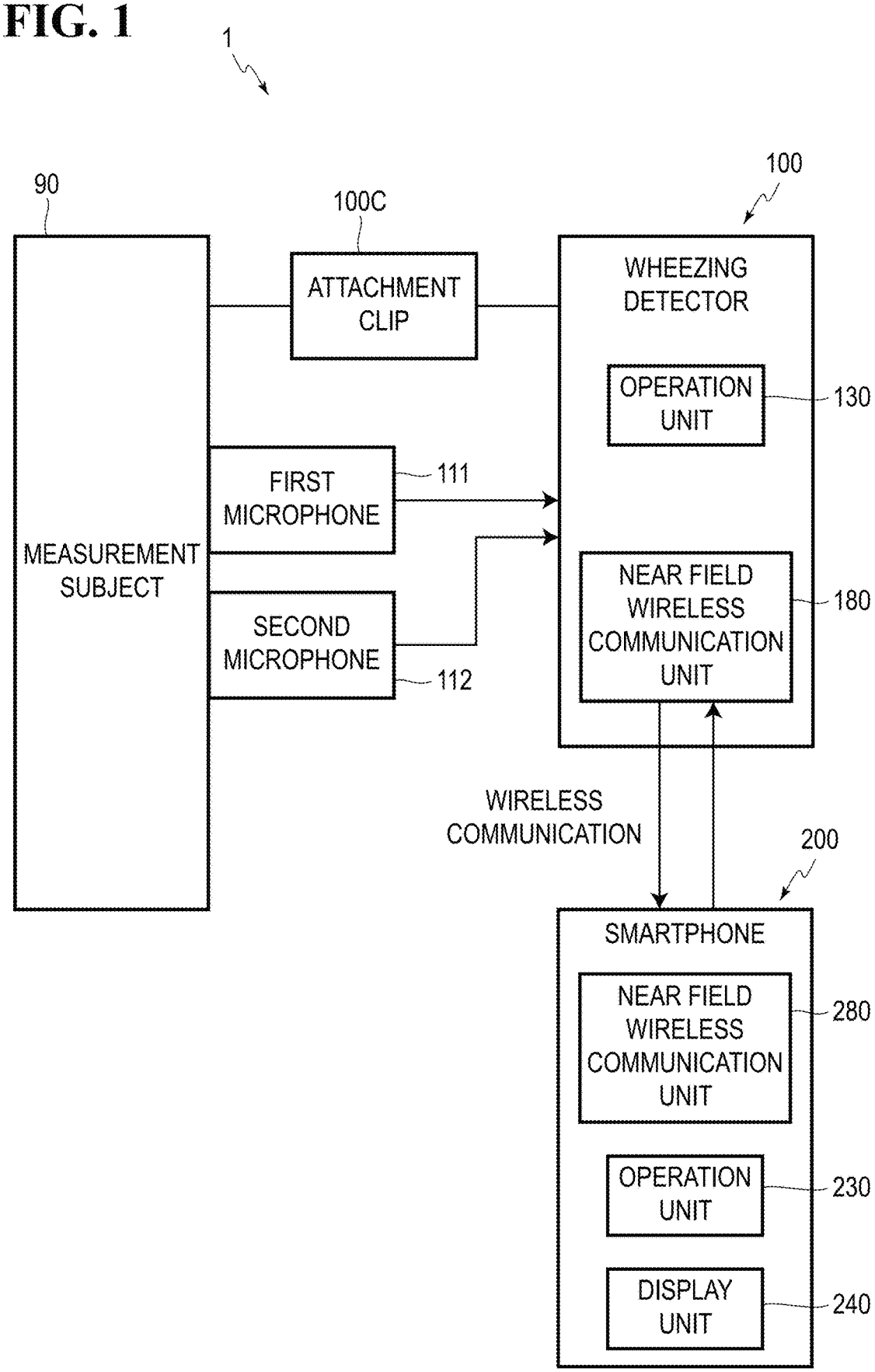
FIG. 1 is a drawing showing a schematic block configuration of a wheezing detection system according to an embodiment of the invention.

FIG. 1 shows a block configuration of a wheezing detection system (indicated overall by reference numeral 1), which is an embodiment of the wheezing detection apparatus of the present invention. The wheezing detection system 1 includes a wheezing detector 100 and a smartphone 200. The wheezing detector 100 and the smartphone 200 can communicate with each other through wireless communication.

Figure 2A:
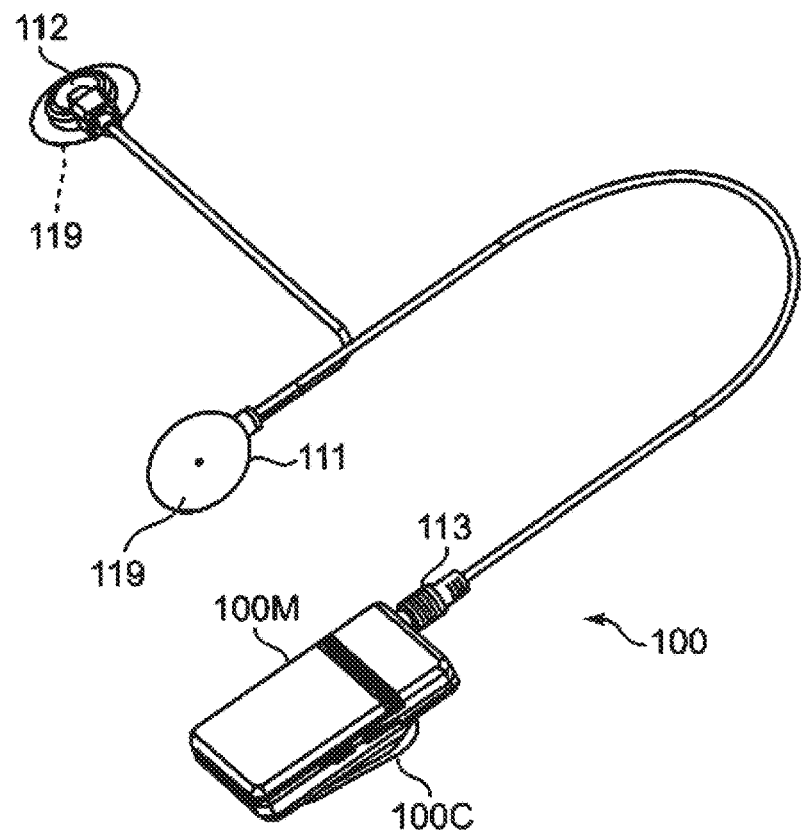
FIG. 2(A) is a diagram showing the exterior of a wheezing detector included in the above-mentioned wheezing detection system.

As shown in FIG. 2(A), the wheezing detector 100 includes a main body 100M, and a first microphone 111 and a second microphone 112 that are joined to the main body 100M via a microphone plug 113. In this example, the first microphone 111 and the second microphone 112 are in the form of stethoscopes that both have circular plate shapes (adhesive sheets 119 being provided on the recessed surfaces thereof). The first microphone 111 is to be adhered to the skin of the chest of the measurement subject, and the second microphone 112 is to be adhered to the clothing of the measurement subject.

Figure 2B:
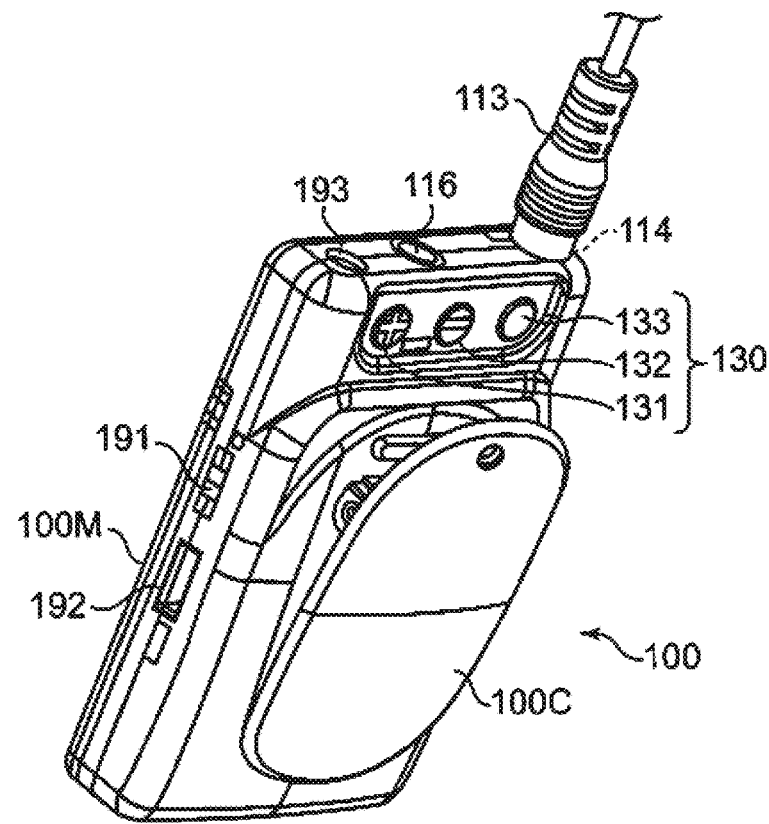
FIG. 2(B) is a diagram showing an enlarged view of the exterior of a main body of the wheezing detector.

As shown enlarged in FIG. 2(B), the main body 100M is provided with a clip 100C, a microphone terminal 114, an operation unit 130, a headphone terminal 116, a power source switch 191, a charging terminal 192, and a communication state display LED (light emitting diode) 193.

The clip 100C is used to attach the main body 100M to the clothing of the measurement subject.

The microphone terminal 114 is used to receive output of the first microphone 111 and the second microphone 112 in a state in which the microphone plug 113 is inserted therein.

The operation unit 130 includes a volume increase button switch 131, a volume decrease button switch 132, and a communication switch 133. The volume increase button switch 131 is used to increase the volume of the sound output to headphones (not shown) via the headphone terminal 116. By contrast, the volume decrease button switch 132 is used to reduce the volume of the sound output to the headphones. The communication switch 133 is used to establish a connection for near field wireless communication between the main body 100M and the smartphone 200. In other words, when the communication switch 133 is pressed, a communication connection between the wheezing detector 100 and the smartphone 200 is established through a known protocol, and near field wireless communication becomes possible.

The power source switch 191 is used to switch on and off the power source of the wheezing detector 100.

The charging terminal 192 is used to charge a battery built into the main body 100M.

The communication state display LED 193 displays the state of communication between the wheezing detector 100 and the smartphone 200. Specifically, if near field wireless communication between the wheezing detector 100 and the smartphone 200 has not been connected, the LED 193 lights up with a red color. If the connection for near field wireless communication between the wheezing detector 100 and the smartphone 200 is in the process of being established, the LED 193 blinks with a green color. If the connection for near field wireless communication between the wheezing detector 100 and the smartphone 200 has been established, the LED 193 lights up with a green color. When the connection for near field wireless communication is established, the wheezing detector 100 enters a state of being able to operate (standby state) according to an instruction from the smartphone 200.

Figure 3:
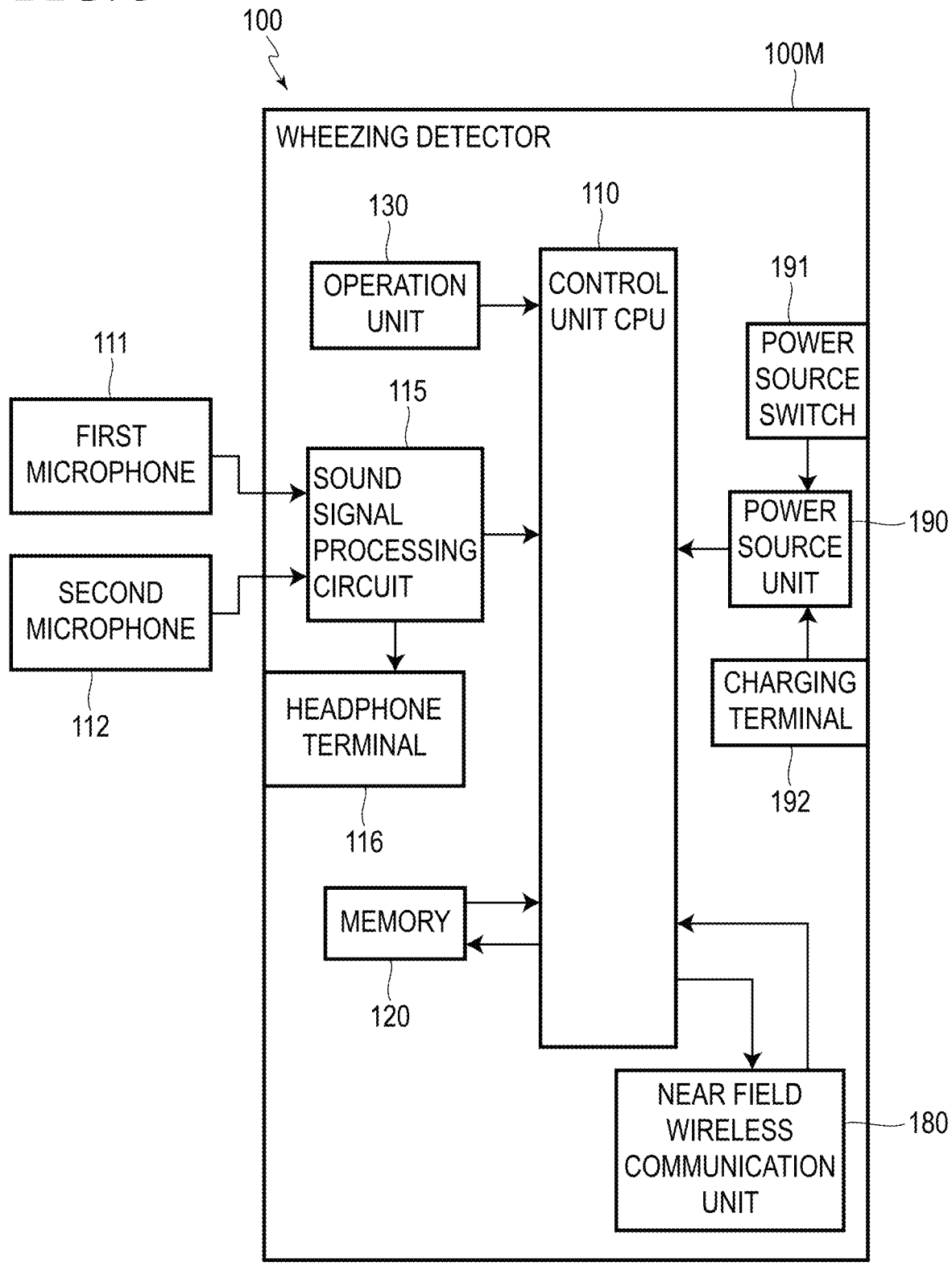
FIG. 3 is a diagram showing a block configuration of the main body of the wheezing detector.

As shown in FIG. 3, the main body 100M of the wheezing detector 100 is provided with a control unit 110, a sound signal processing circuit 115, a memory 120, a near field wireless communication unit 180, and a power source unit 190 in addition to the above-mentioned headphone terminal 116, the operation unit 130, the power source switch 191, and the charging terminal 192.

In this example, the sound signal processing circuit 115 is composed of a CODEC-IC (CODEC integrated circuit), receives the output of the first microphone 111 and the output of the second microphone 112, subtracts the output of the second microphone 112 from the output of the first microphone 111, and outputs a breathing sound signal indicating the obtained difference to the control unit 110 and the headphone terminal 116. The user can confirm that the breathing sound signal has been obtained by connecting headphones (not shown) to the headphone terminal 116 and listening. Note that the first microphone 111, the second microphone 112, and the sound signal processing circuit 115 constitute a breathing sound detection unit.

The memory 120 includes a ROM (Read Only Memory) and a RAM (Random Access Memory). The ROM stores data of programs for controlling the wheezing detector 100. Also, the RAM stores setting data for setting various functions of the wheezing detector 100, data for a calculation result, and the like.

The control unit 110 includes a CPU (Central Processing Unit) and controls the units (including the memory 120 and the near field wireless communication unit 180) of the wheezing detector 100 in accordance with a program for controlling the wheezing detector 100, which is stored in the memory 120. In particular, the control unit 110 determines whether or not wheezing is included in the breathing sound of the measurement subject and creates image data indicating temporal change in the frequency of wheezing (this will be described in detail later).

In this example, the power source unit 190 includes a lithium ion battery (secondary battery) and supplies or stops supplying power to the units of the wheezing detector 100 according to switching on/off of the power source switch 191. The lithium ion battery can be charged via the charging terminal 192.

The near field wireless communication unit 180 performs wireless communication, and in this example, performs near field wireless communication (BT (Bluetooth (registered trademark)) communication and BLE (Bluetooth low energy) communication) with the smartphone 200 in accordance with control performed by the control unit 110. For example, information expressing a calculation result and the like is transmitted to the smartphone 200. Also, an operation instruction is received from the smartphone 200.

Figure 4:
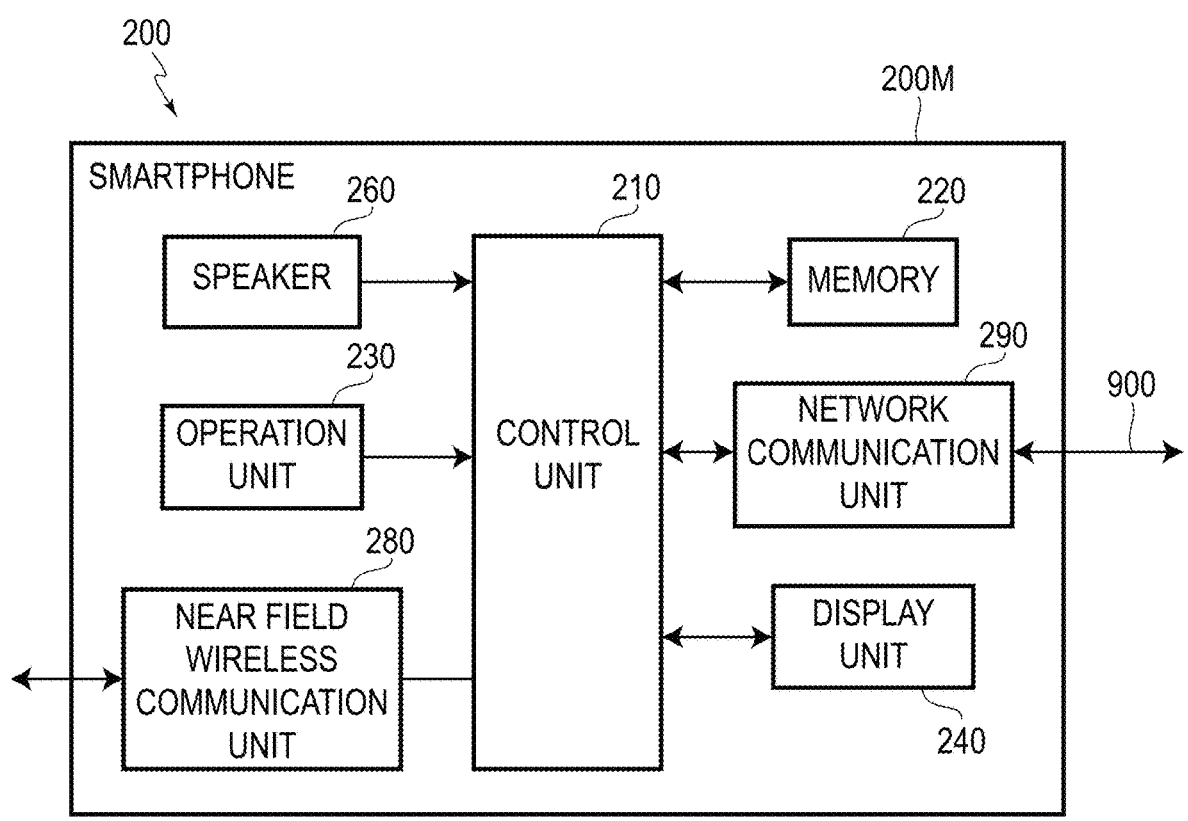
FIG. 4 is a diagram showing a block configuration of a smartphone included in the wheezing detection system.

As shown in FIG. 4, the smartphone 200 includes a main body 200M, a control unit 210 mounted in the main body 200M, a memory 220, an operation unit 230, a display unit 240, a speaker 260, a near field wireless communication unit 280, and a network communication unit 290. The smartphone 200 has application software (referred to as a "wheezing checker" program) installed therein so as to cause a commercially-available smartphone to execute processing of information related to wheezing.

The control unit 210 includes a CPU and auxiliary circuits thereof, controls the units of the smartphone 200, and executes processing in accordance with a program and data stored in the memory 220. For example, based on an instruction input via the operation unit 230, the data input from the communication units 280 and 290 is processed, and the processed data is stored in the memory 220, displayed on the display unit 240, and is output via the communication units 280 and 290.

The memory 220 includes a RAM that is used as a work area needed for a program to be executed by the control unit 210, and a ROM for storing basic programs to be executed by the control unit 210. Also, a semiconductor memory (memory card, SSD (Solid State Drive)) or the like may be used as the storage medium of the auxiliary storage apparatus for assisting the storage region of the memory 220.

In this example, the operation unit 230 is composed of a touch panel provided on the display unit 240. Note that a keyboard or other hardware operation device may be included.

In this example, the display unit 240 includes a display screen composed of an LCD (liquid crystal display element) or an organic EL (electroluminescence) display. The display unit 240 displays various images on the display screen in accordance with control performed by the control unit 210.

The speaker 260 generates various sounds such as audio and an alarm sound serving as a warning, in accordance with control performed by the control unit 210.

The near field wireless communication unit 280 performs wireless communication, and in this example, near field wireless communication (BT communication and BLE communication) with the wheezing detector 100 in accordance with control performed by the control unit 210. For example, an operation instruction is transmitted to the wheezing detector 100. Also, information or the like indicating the calculation result is received from the wheezing detector 100.

The network communication unit 290 can transmit the information from the control unit 210 to another apparatus via the network 290, receive information transmitted via the network 900 from another apparatus, and transfer the received information to the control unit 210.

Figure 5A:
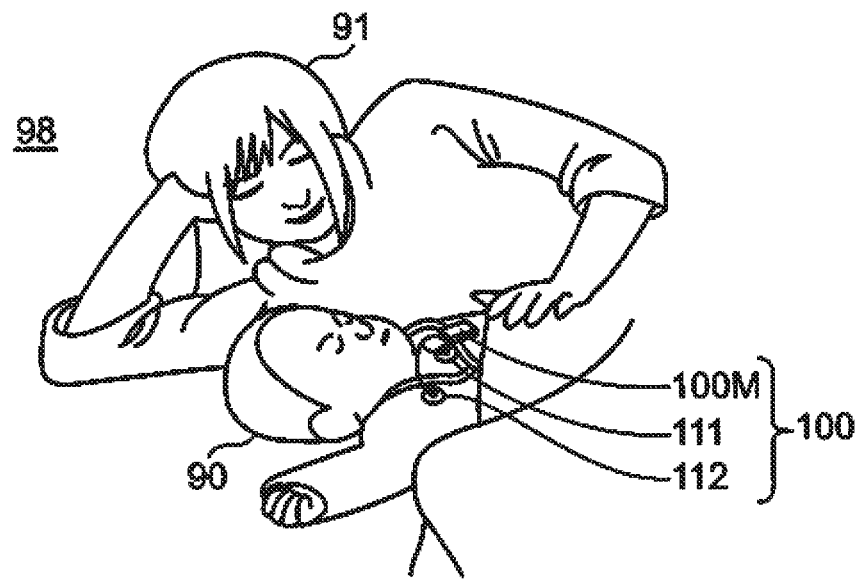
FIG. 5(A) is a diagram showing a mode in which the wheezing detector is attached to an infant serving as a measurement subject.

FIG. 5(A) illustrates a mode in which the wheezing detector 100 is attached to an infant 90 serving as the measurement subject. In this example, the infant 90 is laying down in a child's room 98, and the main body 100M of the wheezing detector 100 is attached to a sleeve of the clothing (in this example, pajamas) of the infant 90 via the clip 100C (see FIG. 2). The first microphone 111 is attached to the skin of the chest of the infant 90 with an adhesive sheet 119 provided on a circular plate. Also, the second microphone 112 is attached to the clothing (in this example, pajamas) of the infant 90. Note that the second microphone 112 may be attached to the skin of a part (a part having little influence on the breathing sound, such as a shoulder) located away from the chest and the respiratory organ of the infant 90.

First Operation Example

Figure 12:
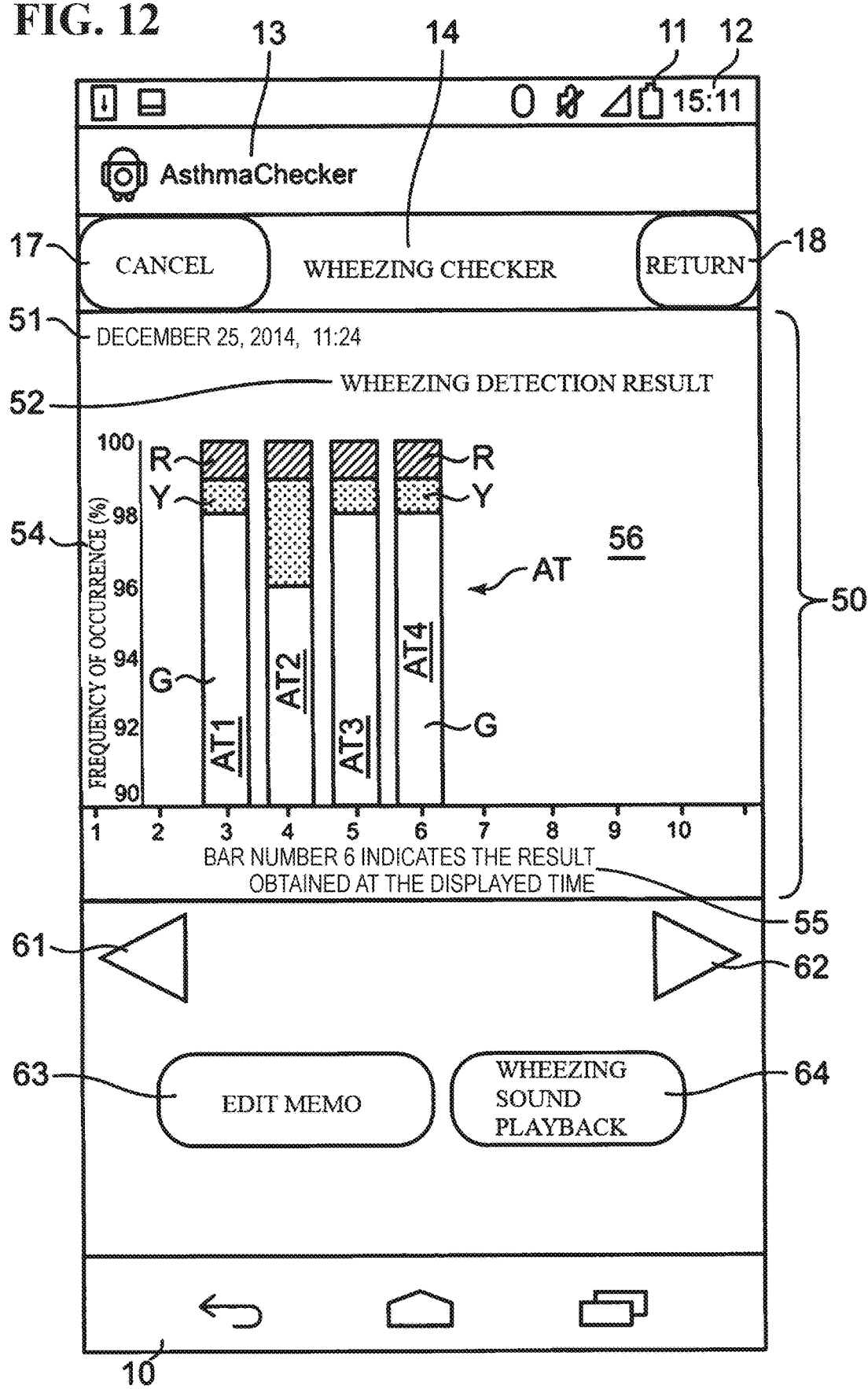
FIG. 12 is a diagram showing an example in which a bar graph expressing temporal change in the frequency of wheezing is displayed on a display screen of a smartphone.
Figure 17:
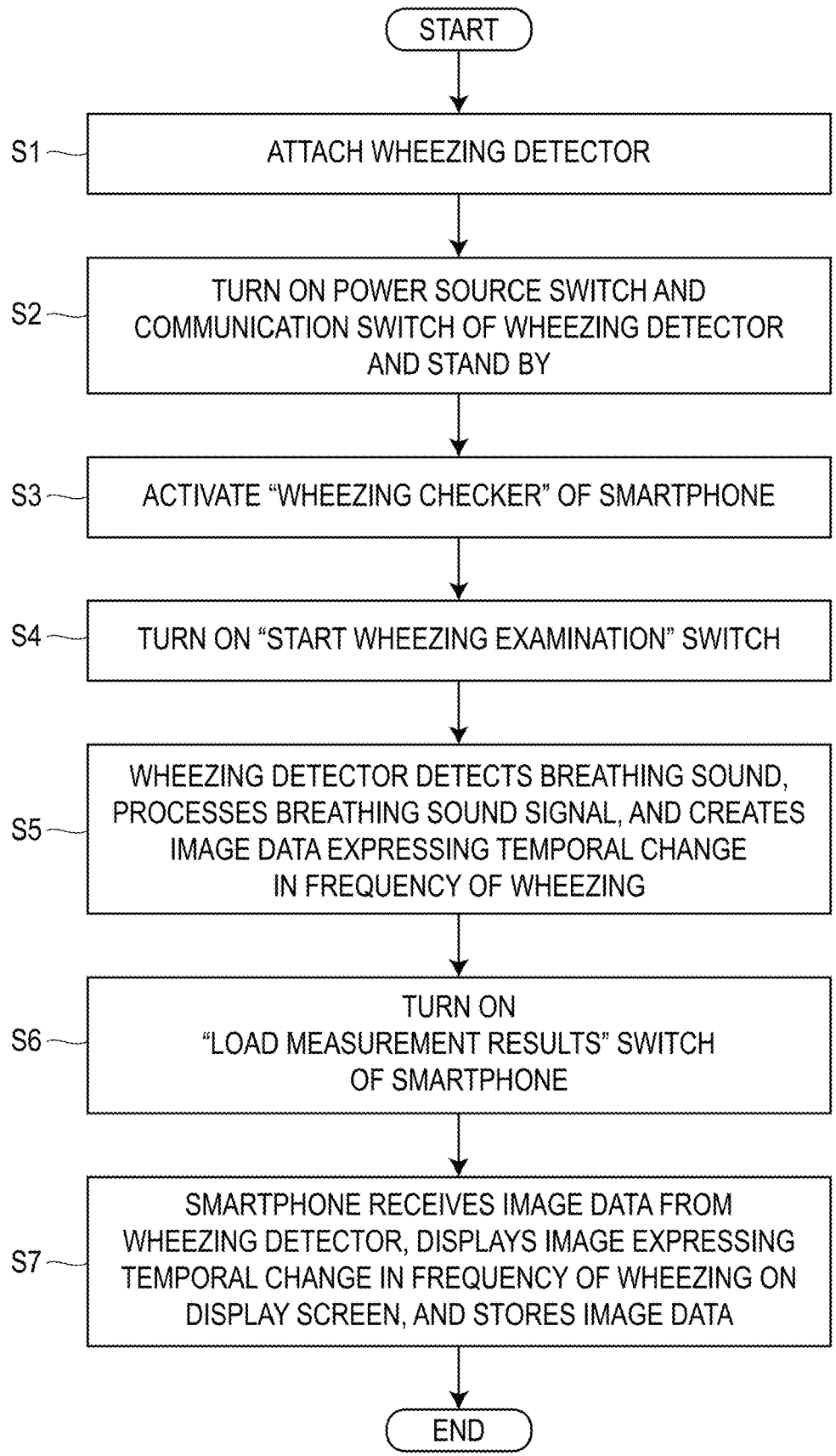
FIG. 17 is a flowchart showing a procedure of operations performed by a user in the case of displaying the display example shown in FIG. 12 on the display screen of the smartphone.

FIG. 17 shows an operation procedure by which the user (in this example, the mother of the infant 90) 91 uses the wheezing detection system 1 to cause the display screen of the smartphone 200 to display a temporal change in the frequency of wheezing of the infant 90 (in this example, bar graph AT shown in FIG. 12).

(1) The user 91 attaches the wheezing detector 100 to the infant 90 as shown in FIG. 5(A) (step S1 in FIG. 17), presses the power source switch 191 and the communication switch 133 of the wheezing detector 100, and puts the wheezing detector 100 in the standby state (step S2 in FIG. 17).

Figure 5B:
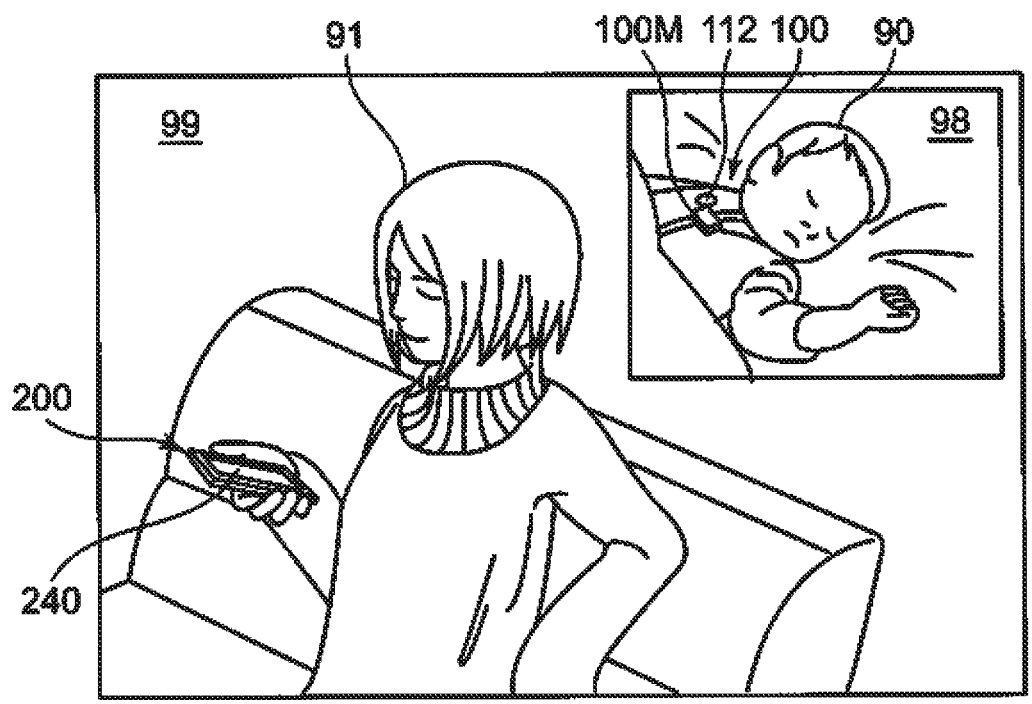
FIG. 5(B) is a diagram showing a mode in which the wheezing detector is operated via the smartphone.

(2) Next, in a living room 99 that is different from the child's room 98, for example, as shown in FIG. 5(B), the user 91 activates a "wheezing checker" program installed in the smartphone 200 (step S3 in FIG. 17). Then, the user 91 presses a "start wheezing examination" switch (indicated by reference numeral 23 in later-described FIG. 15(A)) displayed on the display screen of the smartphone 200, thereby instructing the wheezing detector 100 to start measurement (step S4 in FIG. 17).

(3) Upon doing so, the wheezing detector 100 detects the breathing sound of the infant 90, the breathing sound signal is processed, and image data expressing the temporal change in the frequency of wheezing is created (step S5 in FIG. 17).

i) Specifically, first, the first microphone 111 detects mainly the breathing sound passing through the bronchial tubes of the infant 90, and the second microphone 112 detects mainly environmental sounds in the surroundings of the infant 90. The sound signal processing circuit 115 receives the output of the first microphone 111 and the output of the second microphone 112, subtracts the output of the second microphone 112 from the output of the first microphone 111, and outputs a breathing sound signal (indicated by reference numeral BS) in a time series expressing the obtained difference to the control unit 110. Accordingly, noise components in the surroundings of the infant 90 are removed from the breathing sound signal BS.

Figure 6:
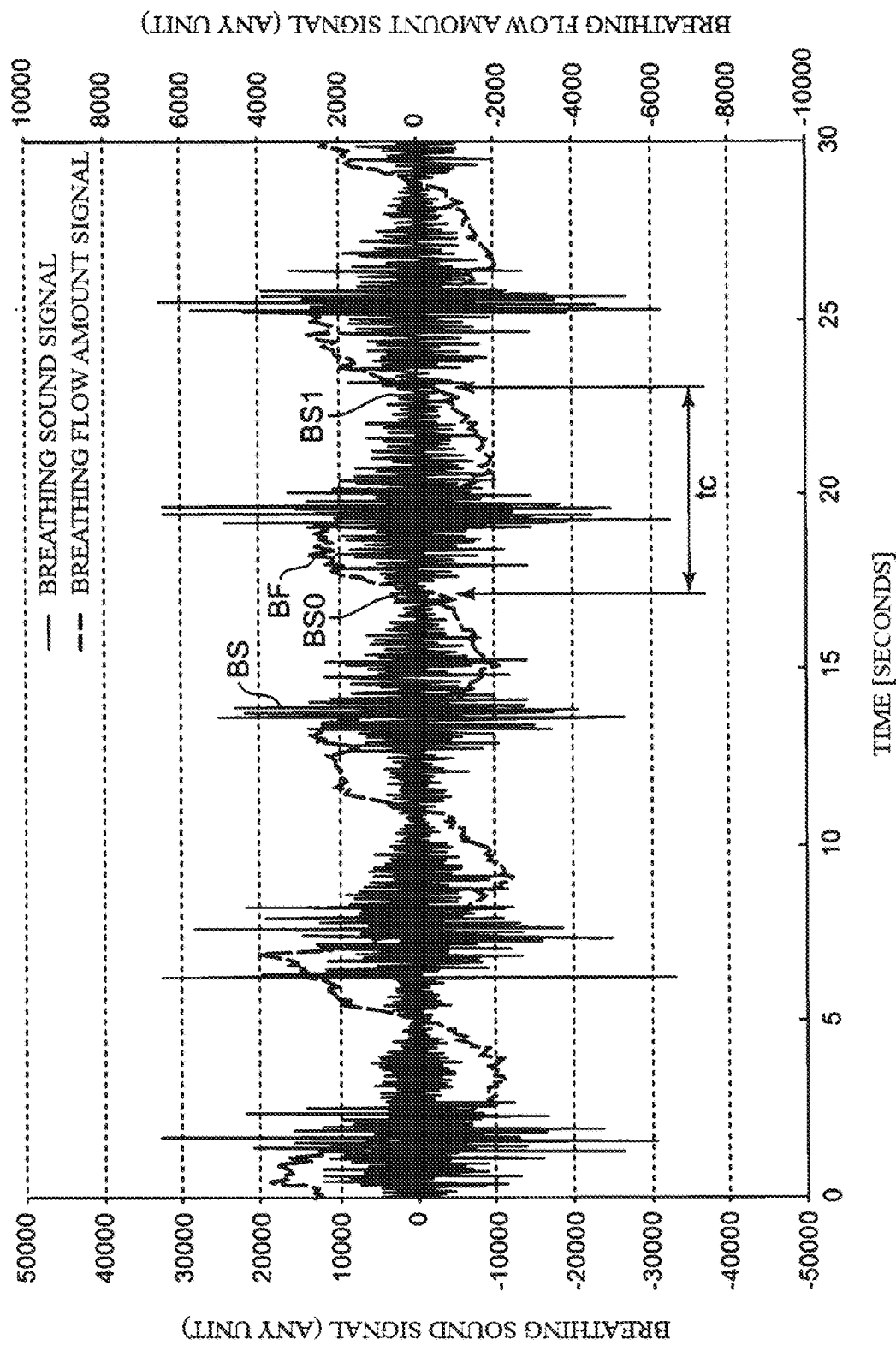
FIG. 6 is a diagram showing both a breathing sound signal detected by a microphone of the wheezing detector and a breathing flow amount signal output by a breathing flow amount sensor.

FIG. 6 illustrates the breathing sound signal BS obtained using the sound signal processing circuit 115 of the wheezing detector 100. Note that in FIG. 6, for the sake of consideration, a breathing flow amount signal BF output by a breathing flow amount sensor (not included in the wheezing detection system 1) is also shown. The positive side of the breathing flow amount signal BF indicates the flow amount for expiration and the negative side indicates the flow amount for inspiration.

ii) Next, the control unit 110 functions as a determination processing unit and determines whether or not wheezing is included in the breathing sound based on the breathing sound signal BS in each predetermined processing unit period (indicated by reference numeral tu; in this example, tu=0.05 seconds).

Figure 7:
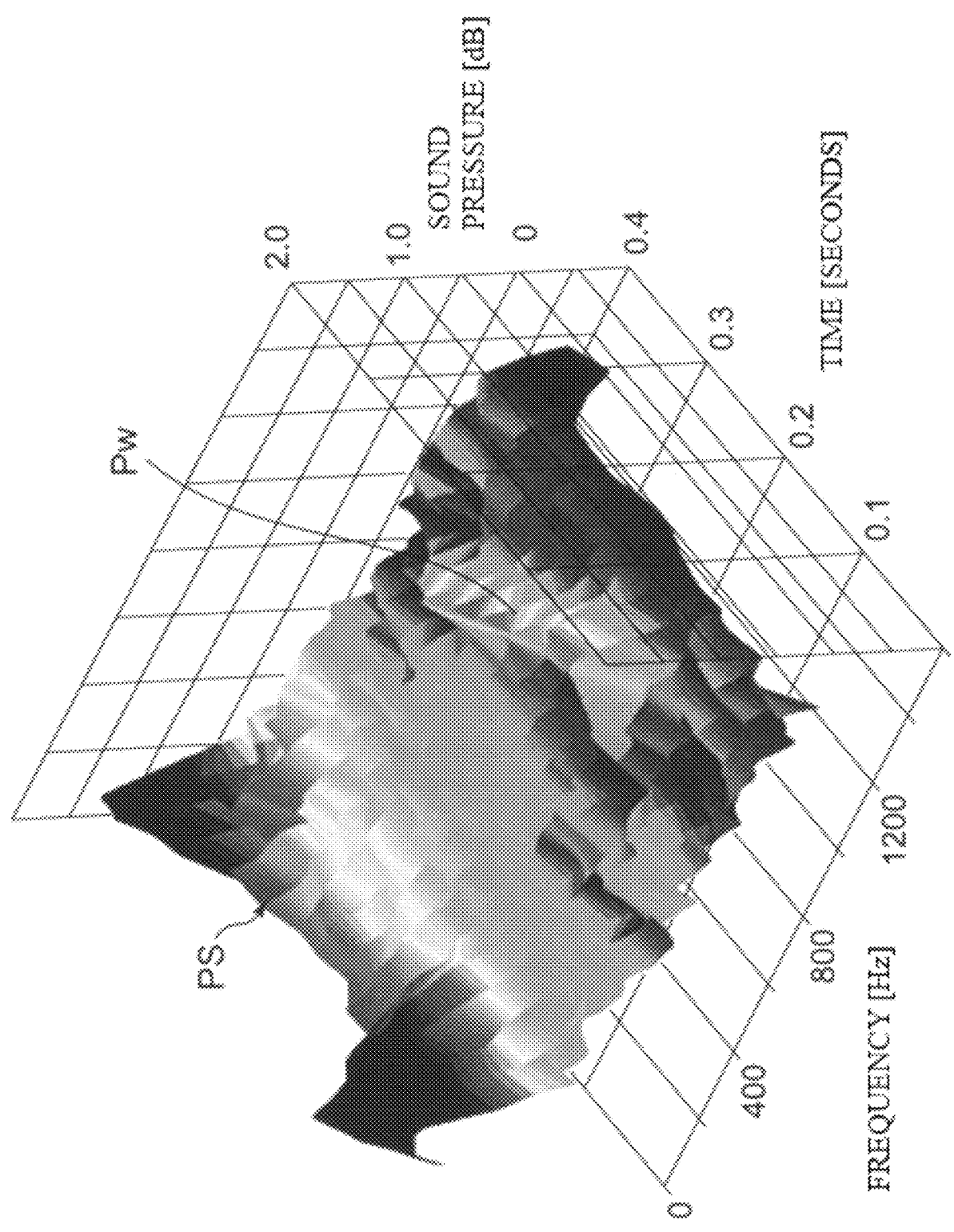
FIG. 7 is a diagram illustrating a frequency spectrum obtained by converting the breathing sound signal into a frequency space.
Figure 8:
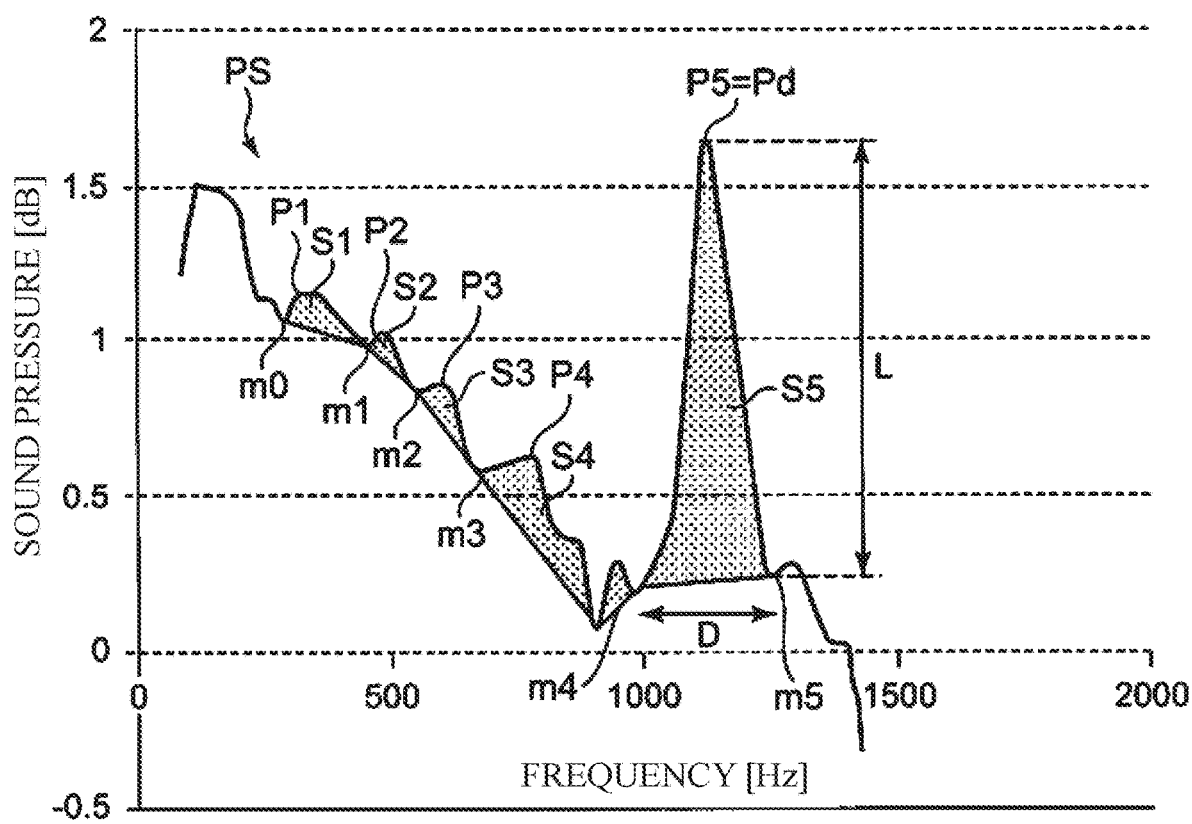
FIG. 8 is a diagram illustrating a frequency spectrum of a breathing sound acquired in a certain processing unit period.

Here, FIG. 7 illustrates a frequency spectrum PS obtained by the control unit 110 converting the breathing sound signal BS into a frequency space in each processing unit period tu. Also, FIG. 8 illustrates a frequency spectrum PS for a breathing sound acquired in a certain processing unit period tu (in this example, corresponds to a processing unit period with a time of 0.05 seconds in FIG. 7). In the analysis performed by the inventor, the whistle-like sound Pw of wheezing (see FIG. 7) is characterized in that, as shown in FIG. 8, the width D of the peak of its frequency spectrum PS is relatively narrow (close to being monotone). Also, the wheezing sound is characterized in that it includes several peaks with relatively narrow widths D (e.g., see FIG. 6 in US 2011/0125044 A1). Accordingly, in order to accurately detect wheezing, the widths D of the peaks in the frequency spectrum PS should be used in the determination in some way. In view of this, with the wheezing detector 100, the control unit 110 determines whether or not a peak in the frequency spectrum PS indicates wheezing based on the height L and the width D of the peak. More specifically, the control unit 110 obtains the ratios between the heights L and the widths D of the peaks (L/D; indicates the steepnesses of the peaks), and determines whether or not wheezing is indicated based on whether or not the ratios (LUD) are greater than a pre-determined first threshold (indicated by reference sign α; in this example, α=0.35).

Note that if background noise exists in the graph of frequency with respect to sound pressure, the heights L and the widths D of the peaks indicate the substantial heights L and the widths D of the peaks from which the background noise has been removed. For example, in the example shown in FIG. 8, it is thought that the heights L and the widths D are the substantial heights L and widths D of peaks P1, P2, P3, P4, and P5, which are portions that exceed line segments connecting local minimums m0, m1, m2, m3, m4, m5, . . . obtained in the graph of frequency with respect to sound pressure. Also, for the later-described areas of the peaks, substantial areas S1, S2, S3, S4, S5, . . . of the portions exceeding the line segments connecting the local minimums are indicated.

In the analysis performed by the inventor, the whistle-like sound Pw (see FIG. 7) of wheezing often observed in the case of infantile asthma is a sound having peaks with relatively narrow widths D (close to being monotone), with a frequency in a range of approximately 900 Hz to 1200 Hz. In view of this, with the wheezing detector 100, the control unit 110 determines whether or not wheezing is indicated only for peaks having frequencies within the range of 200 Hz to 1500 Hz in the frequency spectrum PS. Accordingly, it is possible to detect whether or not wheezing including whistle-like wheezing that is often observed in the case of infantile asthma is included in the breathing sound of a measurement subject, in addition to the wheezing sound. On the other hand, sounds outside of the 200 Hz to 1500 Hz range are not thought of as being wheezing, and therefore are not handled in the determination.

Furthermore, the dominant peak Pd (in this example, peak P5) that has the largest area in the graph of frequency with respect to sound pressure (FIG. 8) among the multiple peaks P1, P2, P3, . . . in the frequency spectrum PS corresponds to the peak with the largest energy. Accordingly, the dominant peak Pd determines whether or not wheezing is included in the processing unit period tu. In view of this, in the wheezing detector 100, the control unit 110 determines whether or not wheezing is indicated based on only the dominant peak Pd that has the largest area in the graph of frequency with respect to sound pressure (FIG. 8) among the multiple peaks P1, P2, P3, . . . in the frequency spectrum PS.

Figure 9:
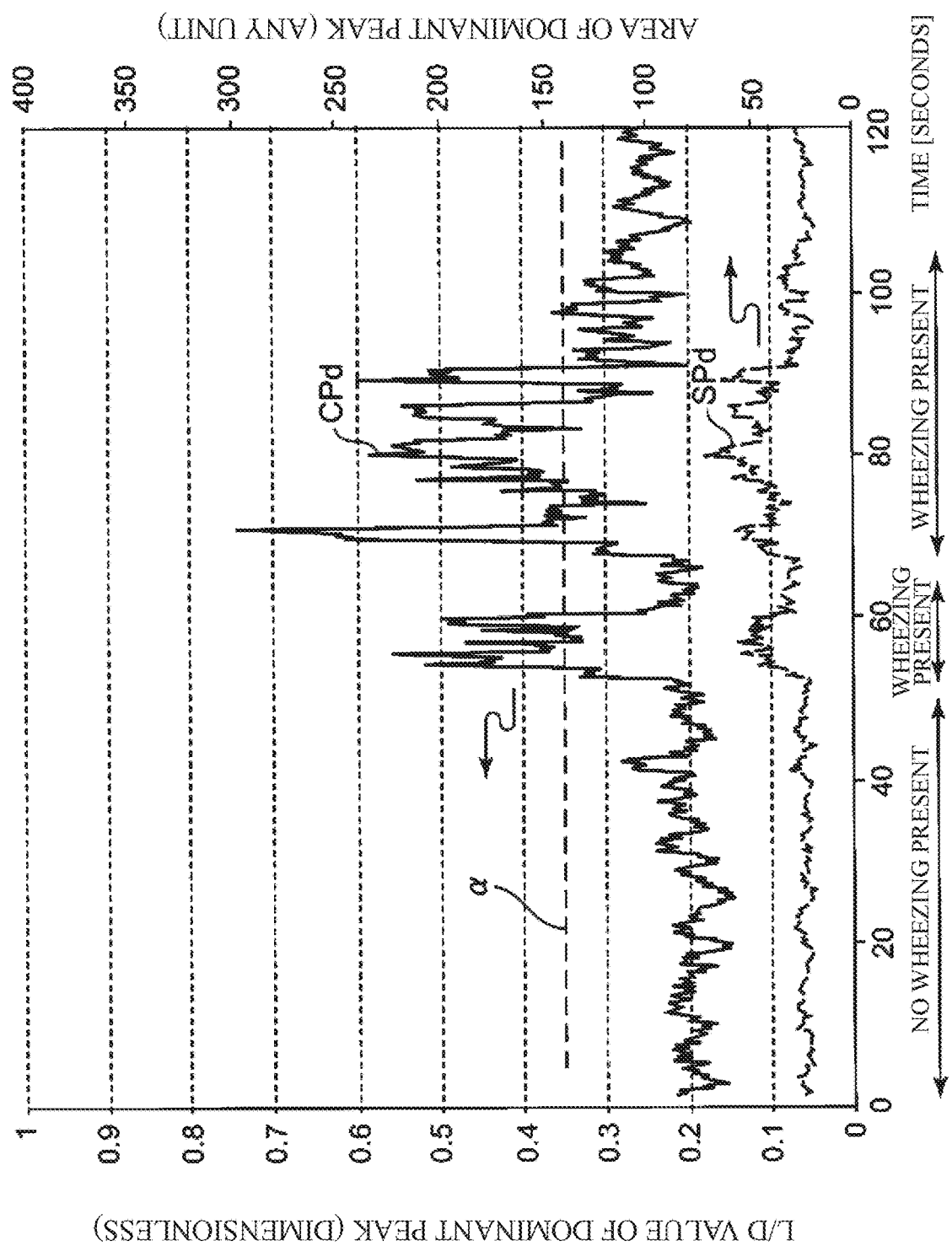
FIG. 9 is a diagram showing both temporal change in an L/D value of a dominant peak included in the frequency spectrum of the breathing sound and temporal change in the area of the dominant peak for a certain asthma patient.

For example, FIG. 9 shows both a temporal change CPd in the IUD value of the dominant peak Pd included in the frequency spectrum of the breathing sound of a certain asthma patient, and a temporal change Spd in the area of the dominant peak Pd. Periods with no wheezing and periods with wheezing that are actually observed are specified on the time axis (horizontal axis). As can be understood from FIG. 9, it is understood that in the periods with no wheezing that were actually observed, the IUD value of the dominant peak Pd is less than or equal to the threshold value $\alpha$, whereas in the periods with wheezing that were actually observed, the L/D value of the dominant peak Pd approximately exceeds the approximate threshold value $\alpha$. Also, accompanying this, in the periods with wheezing, the area of the dominant peak Pd is larger.

Figure 10:
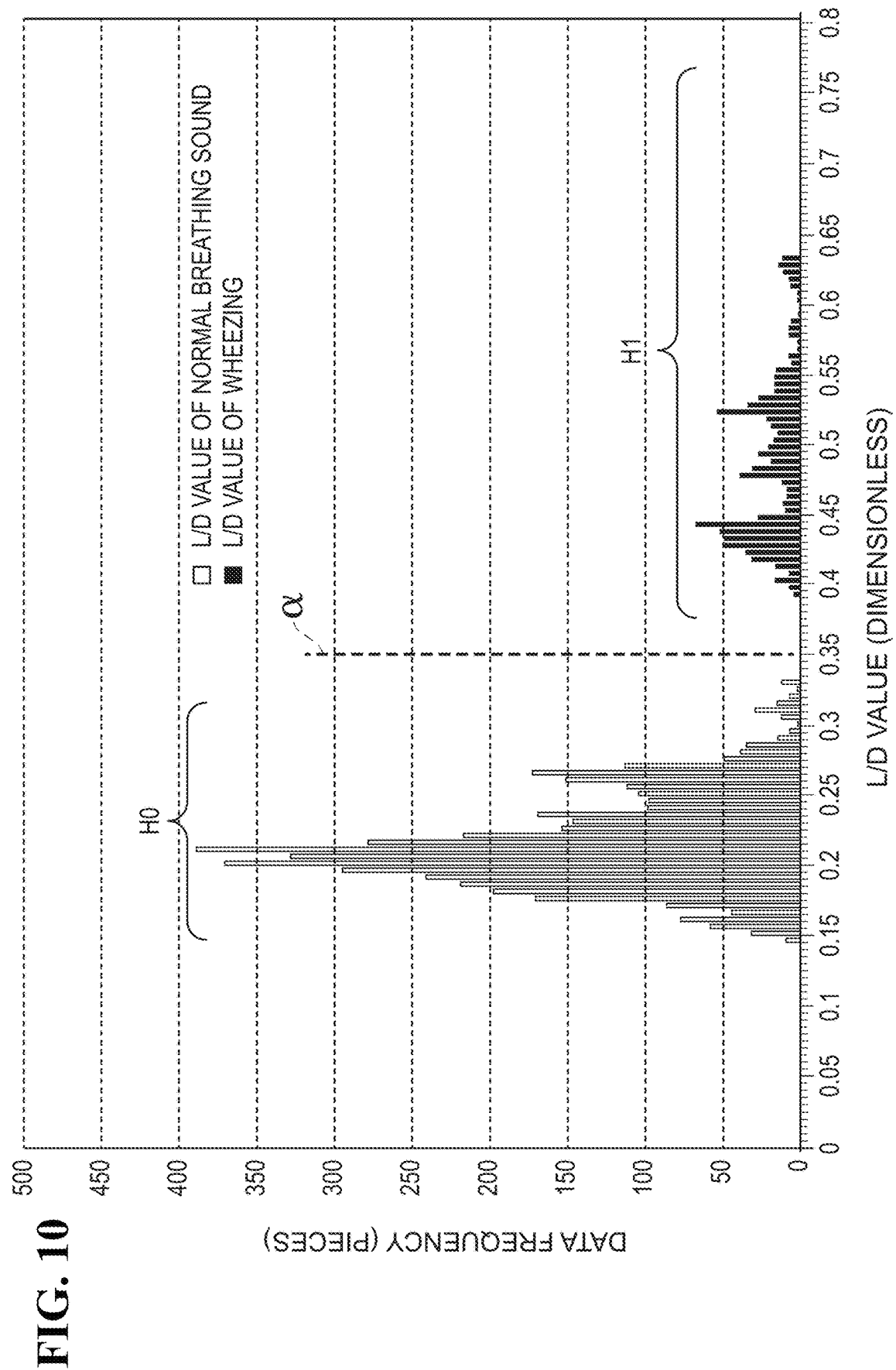
FIG. 10 is a histogram showing the data frequency of L/D values for a normal breathing sound actually observed with no wheezing and the data frequency of LID values for a breathing sound actually observed with wheezing.

Also, FIG. 10 shows, as a histogram, the data frequency of the L/D values for a normal breathing sound actually observed as not including wheezing, and the data frequency of the L/D values for a breathing sound actually observed as including wheezing. As can be understood from FIG. 10, it is understood that data group H0 of L/D values for the normal breathing sound is less than or equal to the threshold value $\alpha$, and data group H1 of L/D values for the breathing sound actually observed as including wheezing exceeds the threshold value $\alpha$.

According to the results shown in FIGS. 9 and 10, it can be said that it is possible to accurately determine whether or not wheezing is included in the breathing sound of the measurement subject with the wheezing detector 100.

The determination results for each processing unit period tu, or in other words, the results of determining whether or not wheezing is included in the breathing sound of the measurement subject are sequentially stored as binary data in the memory 120 and accumulated. For example, if wheezing is included in the breathing sound, 1 is stored, and if wheezing is not included in the breathing sound, 0 is stored.

iii) Next, based on the above-described determination results, the control unit 110 functions as an addition processing unit, sets an addition unit period (e.g., 30 seconds) including multiple processing unit periods tu, and sequentially adds up the lengths of the processing unit periods tu in which it was determined that wheezing was included in an addition unit period.

Figure 11:
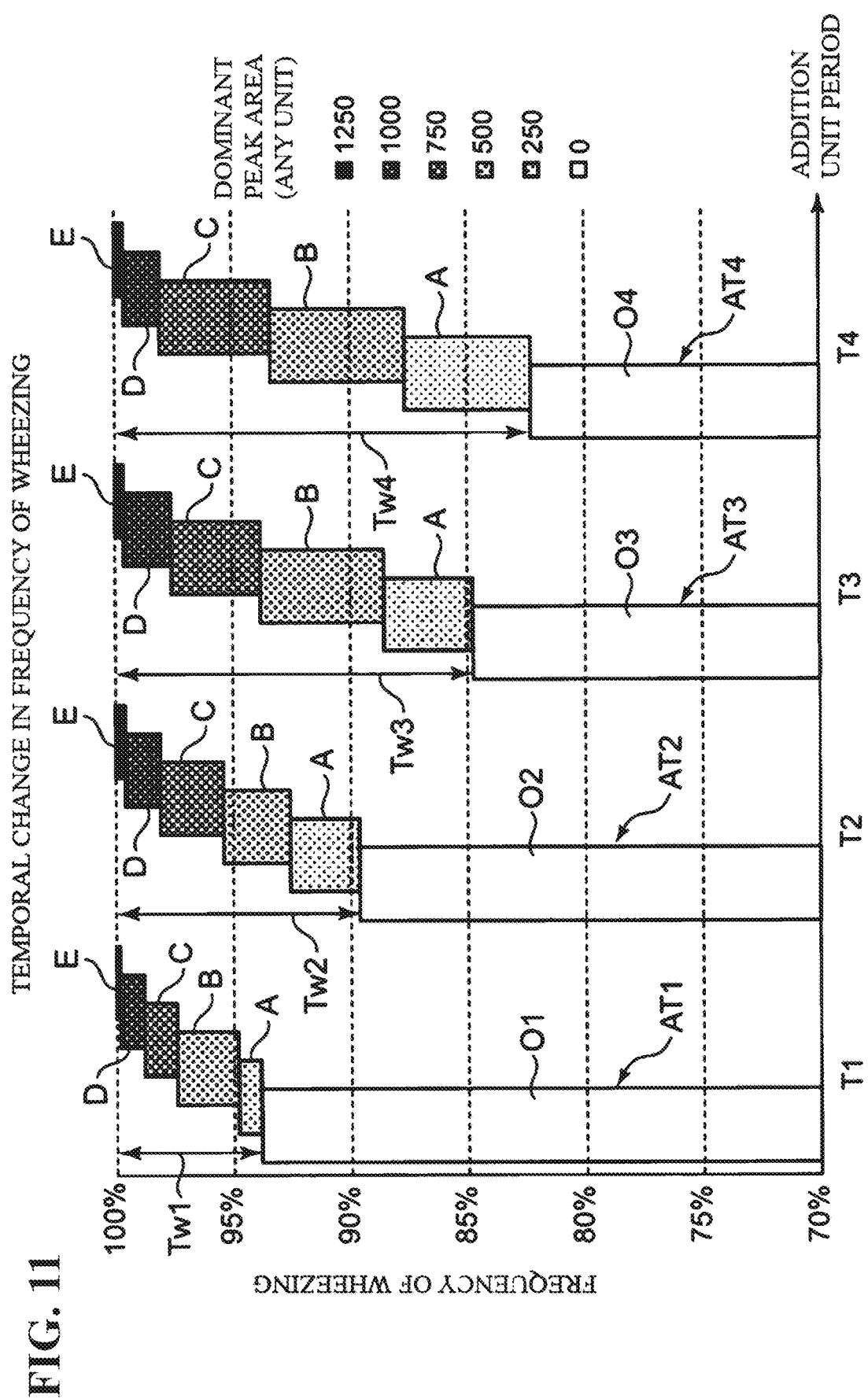
FIG. 11 is a diagram schematically showing a method for expressing temporal change in the frequency of wheezing.

Specifically, as shown schematically in FIG. 11, in each addition unit period T1, T2, T3, T4, . . . , the lengths of the processing unit periods tu that were determined to include wheezing in each a unit period are added up, and the results are obtained as wheezing periods Tw1, Tw2, Tw3, Tw4, . . . . Furthermore, information indicating temporal change in the frequency of wheezing is created as a graph indicating percentages that the wheezing periods Tw1, Tw2, Tw3, Tw4, . . . occupy in bars AT1, AT2, AT3, AT4, . . . having a certain length that corresponds to the addition unit period. Note that the percentages of the periods (normal breathing periods) in which wheezing is not present in the addition unit periods are indicated by O1, O2, O3, O4, . . . .

In particular, in this example, in each addition unit period T1, T2, T3, T4, . . . , the power of the wheezing sound is classified into five levels A, B, C, D, and E based on the area (S5 in the example shown in FIG. 8) of the dominant peak Pd in the frequency spectrum Ps of the breathing sound, and the lengths of the processing unit periods tu that were determined to include wheezing are added up for each of the classified levels A, B, C, D, and E. Level A is set such that the area of the dominant peak Pd is 0 or more and less than 250, level B is set such that the area of the dominant peak Pd is 250 or more and less than 500, level C is set such that the area of the dominant peak Pd is 500 or more and less than 750, level D is set such that the area of the dominant peak Pd is 750 or more and less than 1000, and level E is set such that the area of the dominant peak Pd is 1000 or more and less than 1250. Note that in the example shown in FIG. 11, in order to facilitate understanding, the percentages of the five levels A, B, C, D, and E are shown shifted sequentially to the right, but they may be shown straight as well.

The levels for classifying the power of the wheezing sound (i.e., the severity of the wheezing) are not limited to the five levels A, B, C, D, and E. For example, it might be easier for an average user who is not a medical professional to intuitively understand that the power of the wheezing sound is classified into three levels.

iv) In view of this, in the case of creating image data that is to be transmitted to the smartphone 200 in actuality, the control unit 110 functions as a display processing unit and sets the percentages obtained by combining the normal breathing periods and the periods in which the area of the dominant peak Pd is in a range of 0 or more and less than 250 to green G. The percentages of the periods in which the area of the dominant peak Pd is in a range of 250 or more and less than 750 are made yellow Y. Also, the percentages of the periods in which the area of the dominant peak Pd is in the range of 750 or more are made red R. In response to this, the bars with certain lengths corresponding to the addition unit periods are displayed divided into three colors, namely green G, yellow Y, and red R. Also, the control unit 110 aligns the multiple bars AT1, AT2, . . . corresponding to the addition unit period in parallel so as to create image data indicating a bar graph (in this example, the bar graph AT shown in FIG. 12) indicating temporal change in the frequency of wheezing.

Note that in the example shown in FIG. 11, the addition unit period was set to be 30 seconds, but there is no limitation to this. The addition unit period can be set in various ways, such as one minute, two minutes, five minutes, 10 minutes, 30 minutes, one hour or more and less than 24 hours, one day, one week, or one month. In the following example, the addition unit period is one hour.

Also, when the percentage of time for which the power of the wheezing sound has reached red R exceeds a predetermined second threshold (indicated by reference sign $\beta$; in this example, $\beta=5[\%]$) in an addition unit period, the control unit 110 functions as a warning generation unit that transmits an alarm signal as a warning to the smartphone 200 via the near field wireless communication unit 180.

(4) Next, the user 91 presses a "load measurement results" switch (indicated by reference sign 28 in later-described FIG. 15(A)) displayed on the display screen of the smartphone 200 and receives the image data from the wheezing detector 100 via the near field wireless communication unit 280 (in particular, BLE communication) (step S6 in FIG. 17). The received data is automatically stored and recorded in the memory 220 serving as the storage unit.

Upon doing so, the bar graph AT indicating the temporal change in the frequency of the wheezing illustrated in FIG. 12 is displayed on the display screen 10 of the smartphone 200.

Here, a battery remaining amount 11 and a current time 12 are displayed at the uppermost level of the display screen 10. Also, below that, an "AsthmaChecker" display 13 is provided as the name of the application software and a "wheezing checker" display 14 is provided. A "cancel" switch 17 for inputting an instruction to end the "wheezing checker" program and a "return" switch 18 for inputting an instruction to return to the screen displayed immediately before the content of the display screen are provided on the left and right of the "wheezing checker" display 14. Furthermore, below that, a wheezing detection result display field 50 for displaying image data received from the wheezing detector 100 is provided.

A measurement time display (in this example, "December 25, 2014, 11:24") 51 that displays the final measurement date and time, a field name display 52 that reads "wheezing detection results", and an image data display region 56 are provided in the wheezing detection result display field 50. An order (in this example, "1, 2, 3, . . . ") 55 of the addition unit periods is displayed on the horizontal axis in the image data display region 56. Also, directly below the horizontal axis, it is indicated that the data on the measurement date and time indicated in the measurement time display 51 is included in the sixth piece of data (bar AT 4) as "number 6 indicates the result obtained at the displayed time". Furthermore, in the image data display region 56, as the vertical axis, the "frequency of occurrence (%)" is displayed in increments of 2%, e.g., 90%, 92%, 94%, . . . , 100%. Also, the bar graph AT indicating the temporal change in the frequency of the above-described wheezing is displayed inside of the image data display region 56.

The bar graph AT includes multiple bars AT1, AT2, . . . with a certain height, which each correspond to the addition unit period (in this example, one hour), in the order of the temporal change. The bars are indicated with three colors, namely green G, yellow Y, and red R. As described above, green G indicates a percentage obtained by combining a normal breathing period and a period in which the area of the dominant peak Pd is 0 or more and less than 250, or in other words, a percentage of time for which there is no or approximately no wheezing, in the addition unit period corresponding to the bar. Yellow Y indicates a percentage of time for which the area of the dominant peak Pd is 250 or more and less than 750, or in other words, a percentage of time for which wheezing is relatively small. Red R indicates a percentage of time for which the area of the dominant peak Pd is 750 or more, or in other words, a percentage of time for which wheezing is relatively large.

By looking at the bar graph AT, the user 91 can intuitively, through vision, find out the temporal change in each addition unit period of the severity of wheezing, along with the temporal change in each addition unit period of the frequency of wheezing.

For example, in the example of the bar graph AT shown in FIG. 12, in addition unit period number "3", the percentage of time obtained by combining yellow Y and red R is about 2%, and therefore it can be understood that there was wheezing for about 1.2 minutes in one hour. Also, since the percentage of time for yellow Y and the percentage of time for red R are each about 1%, it can be understood that there was relatively small wheezing and relatively large wheezing for about the same percentages of time. Also, in addition unit period number "4", the percentage of time obtained by combining yellow Y and red R is about 4%, and therefore it can be understood that there was wheezing for about 2.4 minutes in one hour. Also, the percentage of time for yellow Y is about 3% and the percentage of time for red R is about 1%, and therefore it can be understood that the percentage of time for relatively small wheezing increased to about three times the percentage of time for relatively large wheezing. Also, in addition unit periods number "5" and "6", it can be understood that there has been an approximate return to the state of addition unit period number "3".

Thus, by looking at the bar graph AT, the user 91 can, through vision, intuitively find out the temporal change in each addition unit period of the frequency of wheezing and the severity of wheezing included in the breathing sound of the infant 90 serving as the measurement subject. Also, the information expressing the bar graph AT is automatically stored in the memory 220. Accordingly, by loading the information from the memory 220 and causing the bar graph AT to be displayed on the display screen 10 the next time the infant 90 has a medical examination, the user 91 can show the doctor the temporal change in the frequency of wheezing and the severity of wheezing included in the breathing sound of the infant 90. As a result, the doctor can more easily diagnose whether or not the infant 90 has asthma and the severity of the asthma, and can easily create a treatment plan.

Also, the user 91 can understand whether the asthma is getting worse or better by viewing the state of the temporal change for each addition unit period of the frequency of wheezing and the severity of wheezing in the bar graph AT. For example, if the asthma is getting worse, an advance measure such as administering medication is possible, which leads to preventing the asthma from worsening.

On the display screen 10 of the smartphone 200, a direction key 61 according to which a target period displayed in the wheezing detection result display field 50 is moved up, and a direction key 62 according to which a target period is moved down are provided below the wheezing detection result display field 50. The user can select a target period displayed on the display screen 10 as the wheezing detection result by pressing the direction keys 61 and 62. Also, if the user presses the "edit memo" switch 63, a memo screen (not shown) is opened, and the user can manually input and record what he or she felt upon seeing the wheezing detection results. Also, a "wheezing sound playback" switch 64 will be described later.

When the percentage of time for which the power of the wheezing sound reaches red R in the addition unit period exceeds the predetermined threshold β (=5 [%]), the smartphone 200 receives an alarm signal from the wheezing detector 100 via the near field wireless communication unit 280. Upon receiving the alarm signal, the control unit 210 of the smartphone 200 uses the speaker 260 to generate an alarm sound serving as a warning. With this alarm sound, the user 91 can be made aware of the fact that the symptoms of the infant 90 serving as the measurement subject have worsened, even if the user 91 is in a living room 99 separate from the child's room (where the infant 90 is lying) 98. Accordingly, it is possible to take a countermeasure such as administering medication to the infant 90. The warning is particularly advantageous in the case where the measurement subject is an infant 90, a critically ill patient, or the like, who has difficulty expressing intention.

Note that the warning is not limited to generation of an alarm sound using the speaker 260, and it is also possible to perform alarm display (not shown) on the display screen 10, or vibrate using a vibrator (not shown) that performs notification of signal reception.

Second Operation Example

Figure 18:
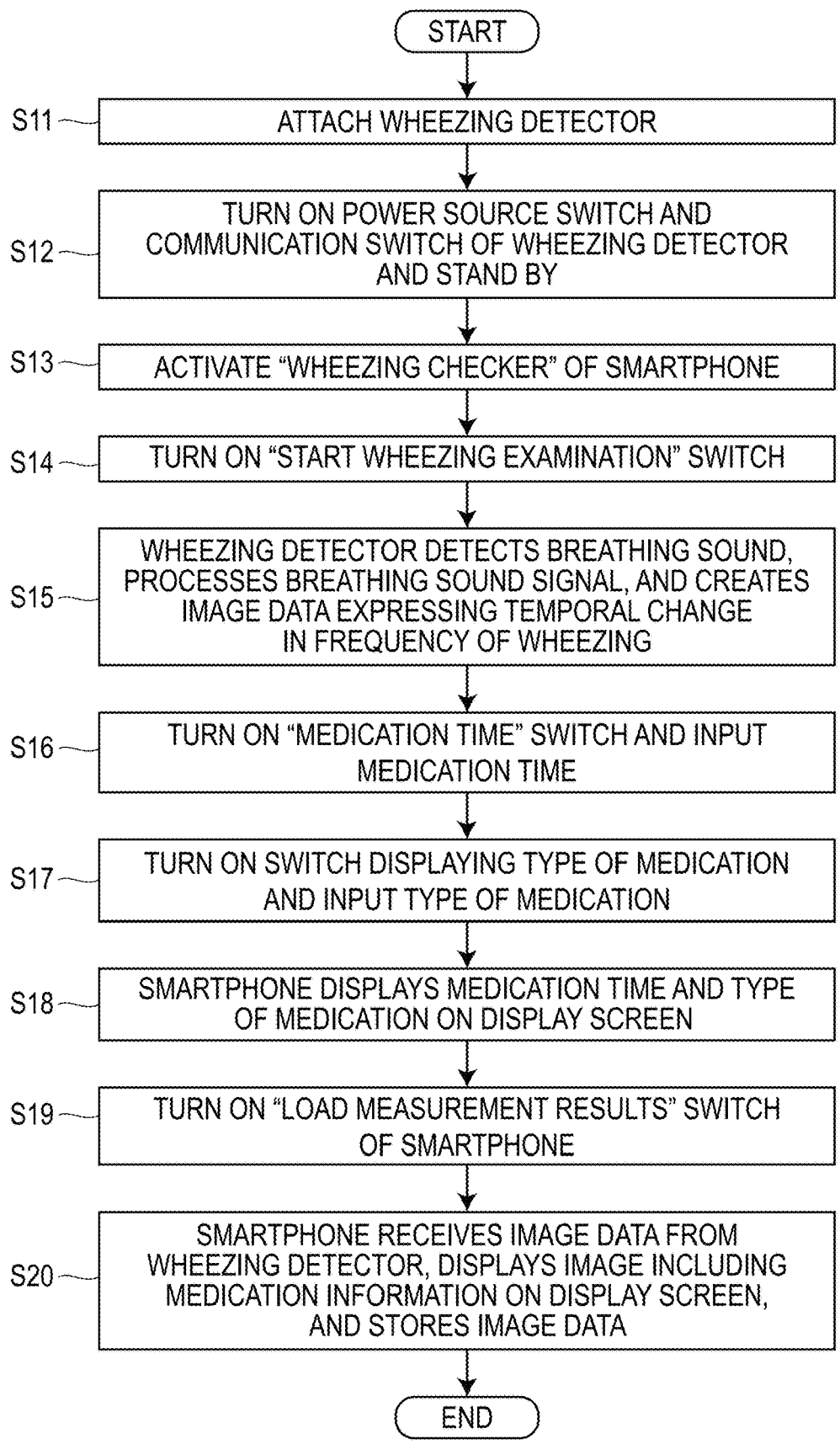
FIG. 18 is a flowchart showing a procedure of operations performed by a user in the case of displaying the display example shown in FIG. 16(B) on the display screen of the smartphone.

FIG. 18 shows an operation procedure for displaying, on the display screen of the smartphone 200, the bar graph AT indicating the temporal change in the frequency of wheezing of the infant 90 and the information relating to administration of medication, according to the wheezing detection system 1.

(1) Steps S11 to S15 in FIG. 18 are carried out similarly to steps S1 to S5 in FIG. 17.

Figure 15A:
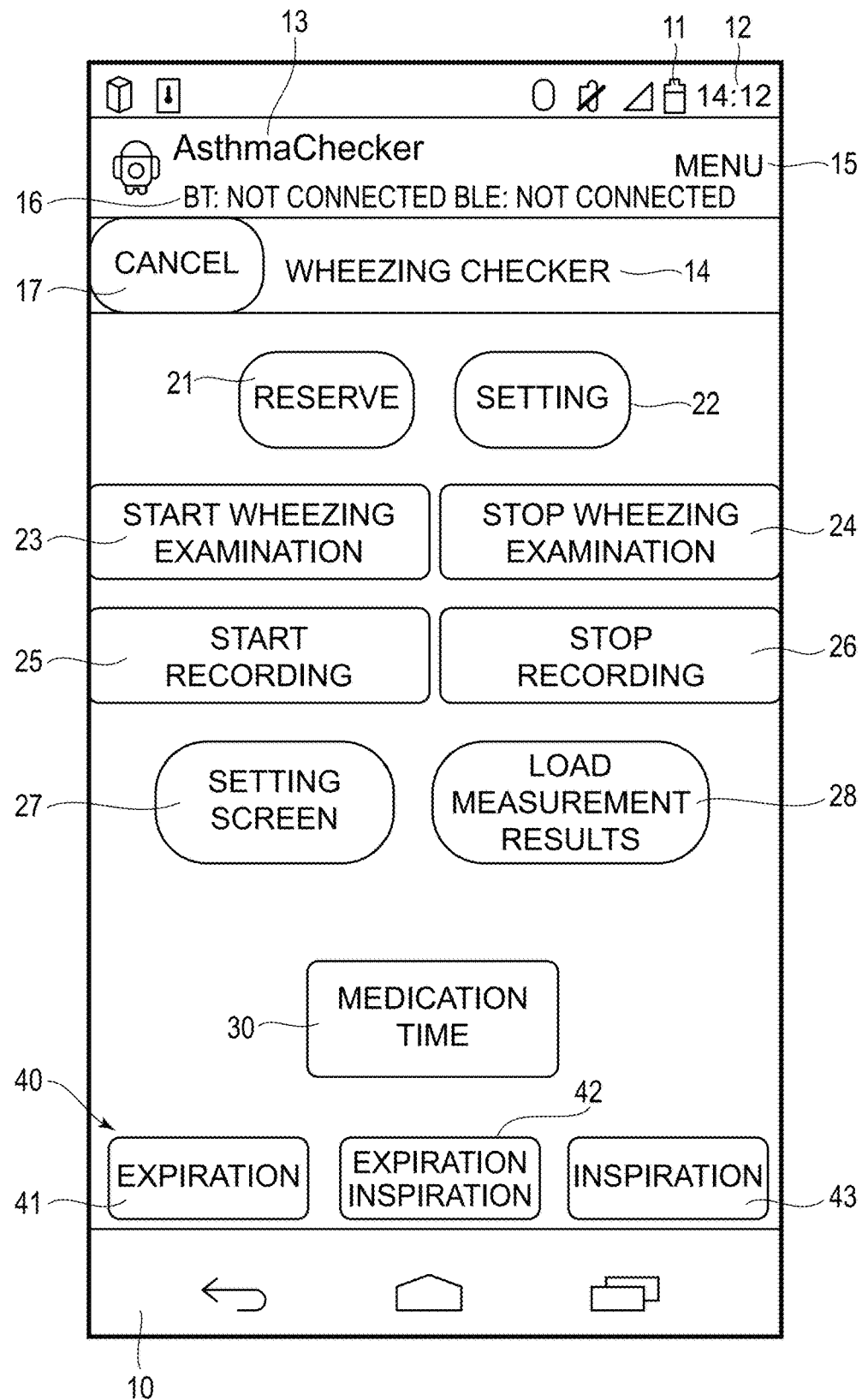
FIG. 15(A) is a diagram showing an initialization menu screen for a "wheezing checker" program installed on the smartphone.

Here, FIG. 15(A) illustrates an initialization menu screen displayed on the display screen 10 when the user 91 activates the "wheezing checker" program installed in the smartphone 200 in step S13 of FIG. 18.

On the initialization menu screen shown in FIG. 15(A), a state 16 of "not connected" or "connected" of BT communication or BLE communication with the wheezing detector 100 performed by the near field wireless communication unit 280 is displayed between the "AsthmaChecker" display 13 and the "wheezing checker" display 14. Also, below the "wheezing checker" display 14, a "reservation" switch 21, a "setting" switch 22, a "start wheezing examination" switch 23, a "stop wheezing examination" switch 24, a "start recording" switch 25, a "stop recording" switch 26, a "setting screen" switch 27, a "load measurement results" switch 28, a "medication time" switch 30, and a phase selection switch 40 serving as a phase instruction input unit are provided.

The "reservation" switch 21 is used in order for the user 91 to reserve a period of time, such as from December 26, 2014, 21:00 to December 27, 2014, 7:00, during which measurement is to be performed by the wheezing detector 100. The "setting" switch 22 is used to set the condition (in this example, the threshold value 13) under which the wheezing detector 100 generates the above-described alarm signal, and to set whether or not to generate the alarm sound, whether or not to perform alarm display, whether or not to perform automatic recording, and the like when the smartphone 200 receives the alarm signal. The "start wheezing examination" switch 23 is used to instruct the wheezing detector 100 to start measurement. The "stop wheezing examination" switch 24 is used to instruct the wheezing detector 100 to stop measurement. The "start recording" switch 25 is used to instruct the wheezing detector 100 to transmit the breathing sound signal BS. The "stop recording" switch 26 is used to instruct the wheezing detector 100 to stop transmitting the breathing sound signal BS. The "setting screen" switch 27 is used to set an SSID (Service Set Identification) and an encryption key (password) between the near field wireless communication unit 280 of the smartphone 200 and the near field wireless communication unit 180 of the wheezing detector 100. The "medication time" switch 30 is used to input a time for administering medication (year, month, day, hour, minute). Note that the phase selection switch 40 will be described later.

Figure 15B:
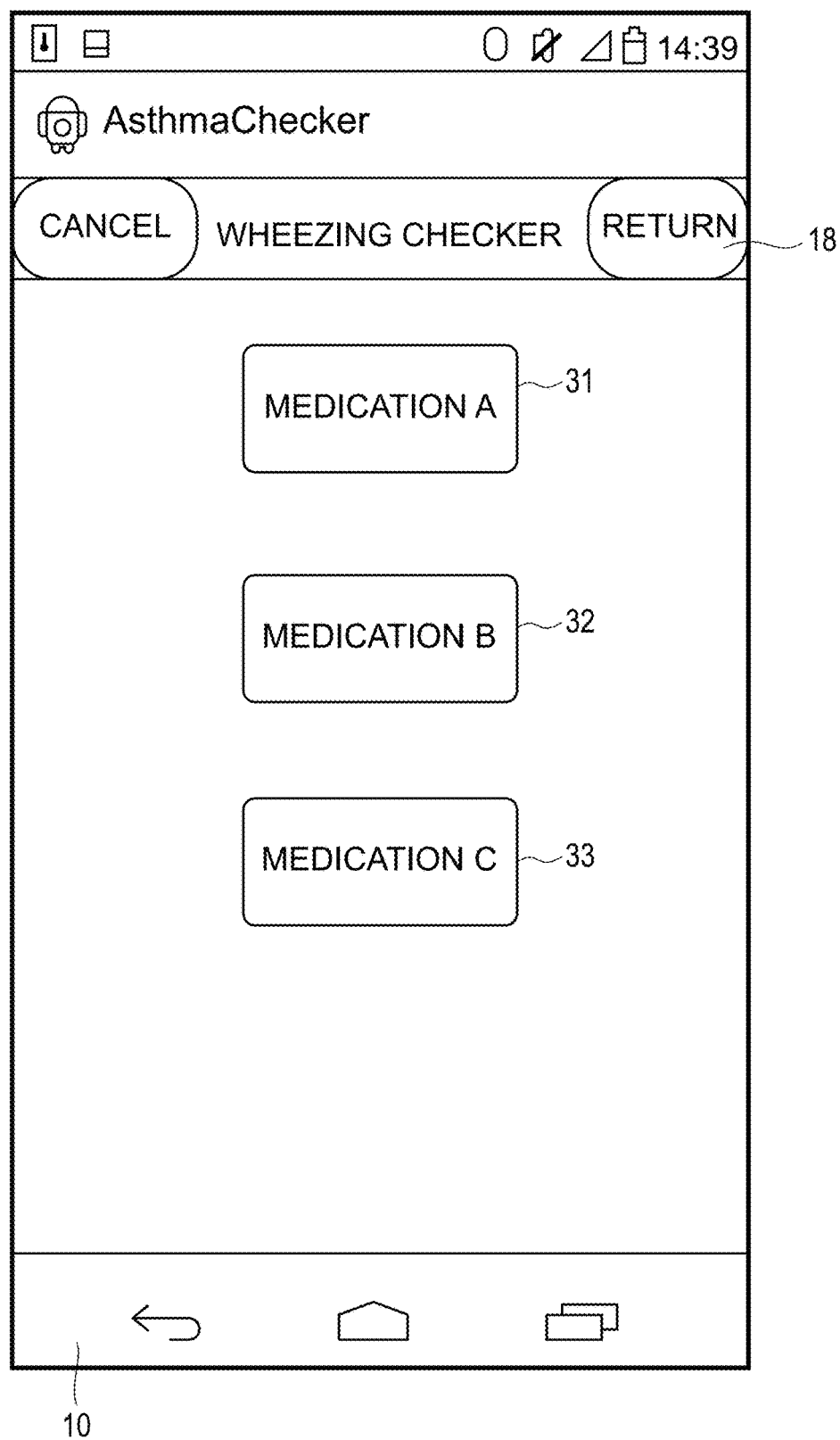
FIG. 15(B) is a diagram showing a screen displayed when a "medication time" switch is pressed in FIG. 15(A).

(2) In this example, in the state in which the initialization menu screen shown in FIG. 15(A) is displayed on the display screen 10 of the smartphone 200, the user 91 presses the "medication time" switch 30 (step S16 in FIG. 18). Upon doing so, the time at which the "medication time" switch 30 was pressed is stored as the medication time (year, month, day, hour, minute) in the memory 220. Note that it is also possible to use a configuration in which when the user 91 presses the "medication time" switch 30, a screen for inputting the medication time opens, the user 91 inputs the medication time (year, month, day, hour, minute) in that screen, and when the user 91 presses the "medication time" switch 30 again, the input medication time is stored. When the medication time is stored, the medication information input screen for inputting the type of medication that was administered, as illustrated in FIG. 15(B), is displayed on the display screen 10. In this example, three types of switches, namely a "medication A" switch 31, a "medication B" switch 32, and a "medication C" switch 33, are displayed. Note that in actuality, specific medication names designated in a prescription by a doctor are registered in advance as the "medication A", "medication B", and "medication C" using a medication name registration screen (not shown). The specific medication names that were registered are displayed in the display locations for "medication A", "medication B", and "medication C" in FIG. 15(B). The switches 30, 31, 32, and 33 constitute medication information input units.

(3) In a state in which the medication information input screen shown in FIG. 15(B) is displayed, the user 91 pushes one of the medication switches and inputs the type of medication (step S17 in FIG. 18). For example, when the user 91 presses the "medication A" switch 31, a screen for checking that includes medication information 34, which says "December 25, 2014, 11:22, administered medication A" is displayed on the display screen 10 of the smartphone 200, as illustrated in FIG. 16(A) (step S18 in FIG. 18).

Figure 16A:
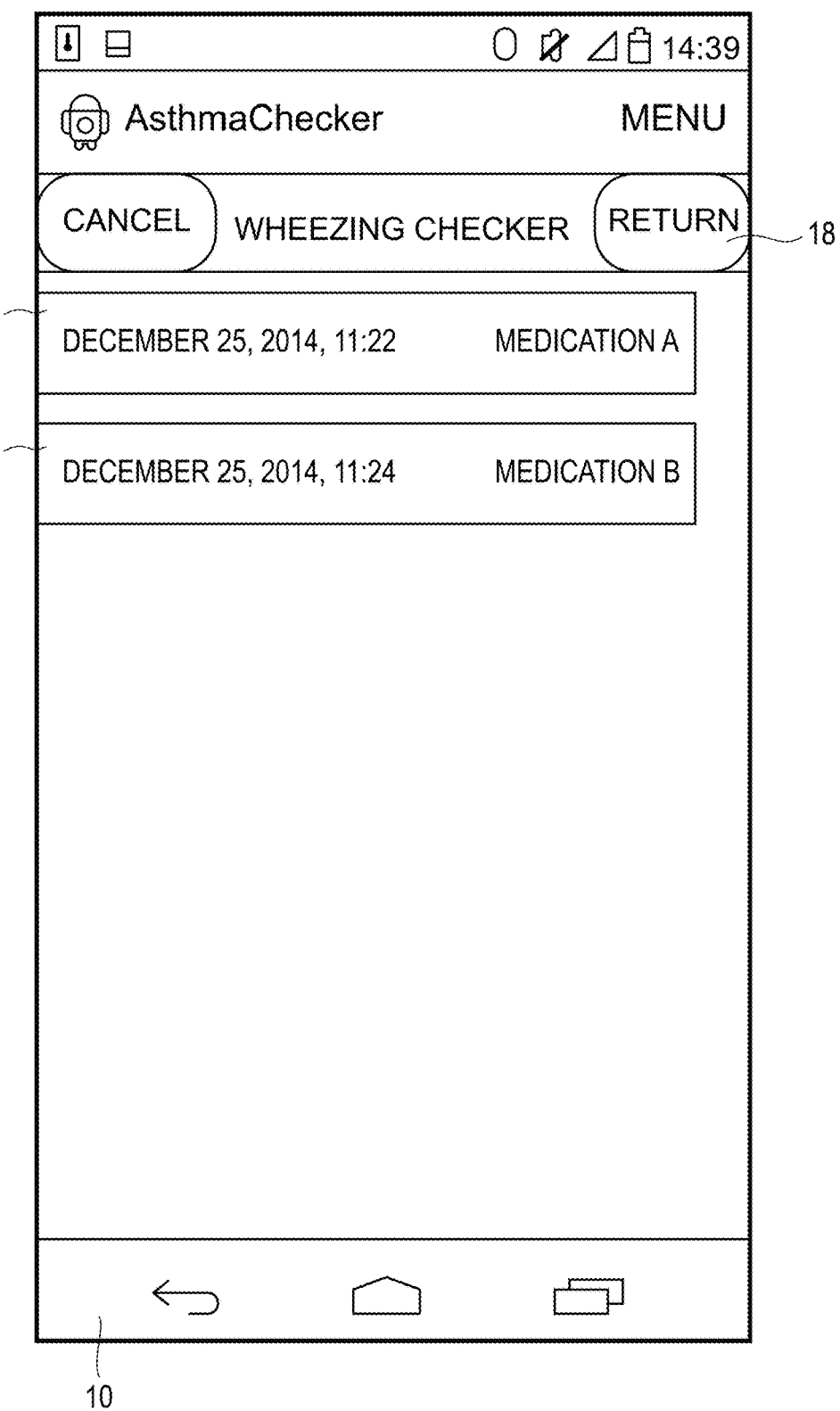
FIG. 16(A) is a diagram showing a screen displayed when a "medication A" switch and a "medication B" switch are pressed in FIG. 15(B).

(4) Furthermore, when the user 91 presses the "return" switch 18 twice to return to the initialization menu screen shown in FIG. 15(A), presses the "medication time" switch 30, and presses the "medication B" switch 32 on the medication information input screen shown in FIG. 15(B), as illustrated in FIG. 16(A), a screen for checking that includes the medication information 35, which says "December 25, 2014, 11:24, administered medication B" is displayed along with the previous medication information 34. In other words, each time medication is administered, steps S16 to S18 in FIG. 18 are repeated.

(5) Thereafter, the user 91 presses the "return" switch 18 twice to return to the initialization menu screen shown in FIG. 15(A), presses the "load measurement result" switch 28 to receive image data from the wheezing detector 100 via the near field wireless communication unit 280 (in particular, BLE communication) (step S19 in FIG. 18). The received data is automatically stored and recorded in the memory 220 serving as the storage unit.

Figure 16B:
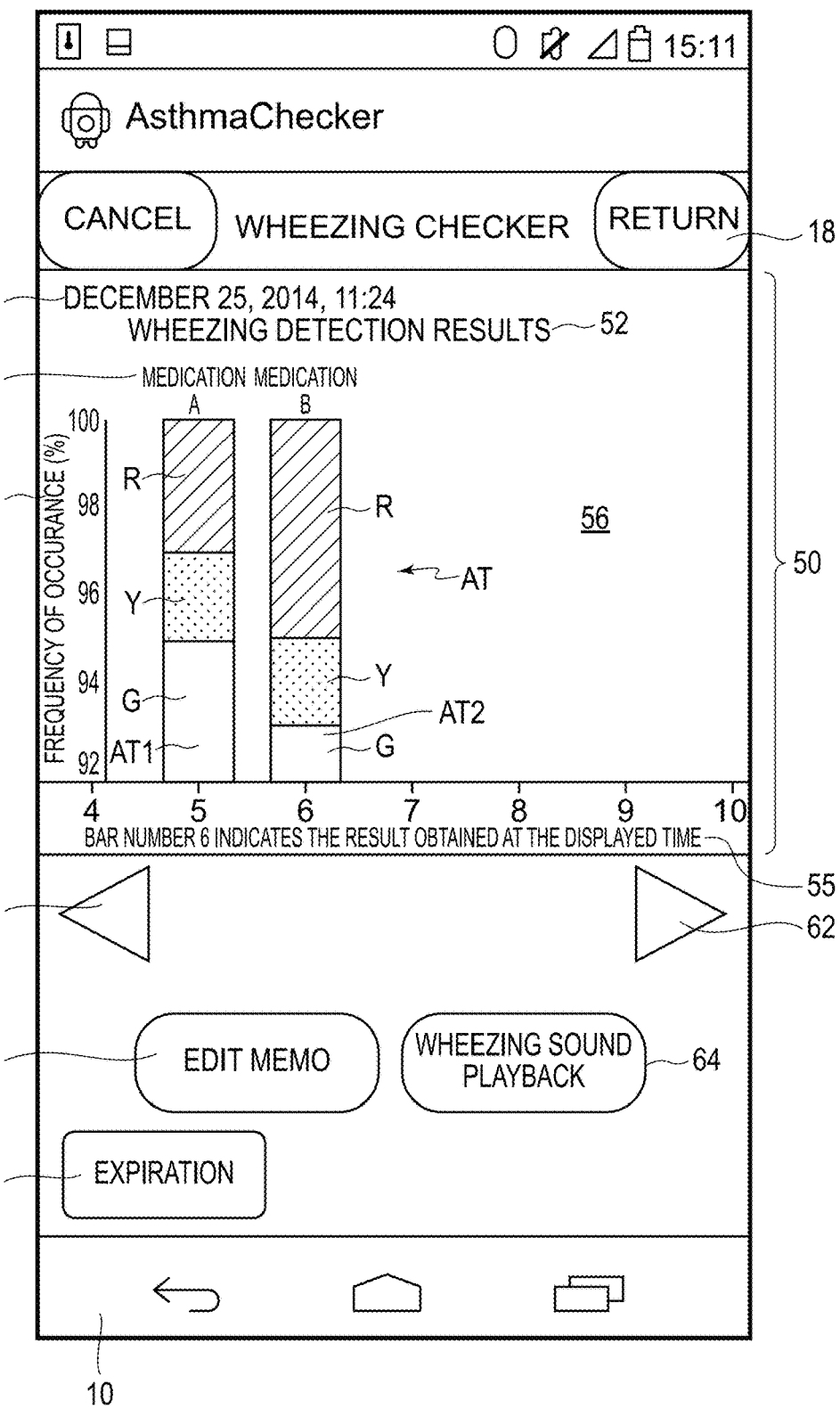
FIG. 16(B) is a diagram showing an example in which both a bar graph indicating temporal change in the frequency of wheezing and information relating to medication are displayed on the display screen of the smartphone.

Upon doing so, the control unit 210 of the smartphone 200 functions as the display processing unit, and as shown in FIG. 16(B), the medication information for each addition unit period is displayed in the display screen 10 along with the bar graph AT indicating the temporal change in the frequency of wheezing (step S20 in FIG. 18). In the example shown in FIG. 16(B), "medication A" is displayed above the bar graph AT1 for the addition unit period number 5, and "medication B" is displayed above the bar graph AT1 for addition unit period number 6. The user 91 can, through vision, intuitively find out the frequency of wheezing in the addition unit period, information relating to medication, and in this example, find out that the medication A was given to the infant 90 in addition unit period number 5 and that the medication B was given to the infant 90 in addition unit period number 6. Accordingly, the user 91 or the doctor who has been shown the screen shown in FIG. 16(B) can easily determine whether or not the medication had an effect (a decrease in the frequency of wheezing) on the infant 90.

For example, in the example shown in FIG. 16(B), regardless of the fact that there was "medication A" in the addition unit period number 5 (where the percentage of the red R time was about 3%), the percentage of the red R time increased to about 5% in addition unit period 6, and the symptoms of the infant 90 worsened. For this reason, there is a high likelihood that "medication A" was not effective. It might be better to determine the effect of "medication B" after viewing addition unit period number 7 and onward.

Third Operation Example

Figure 19:
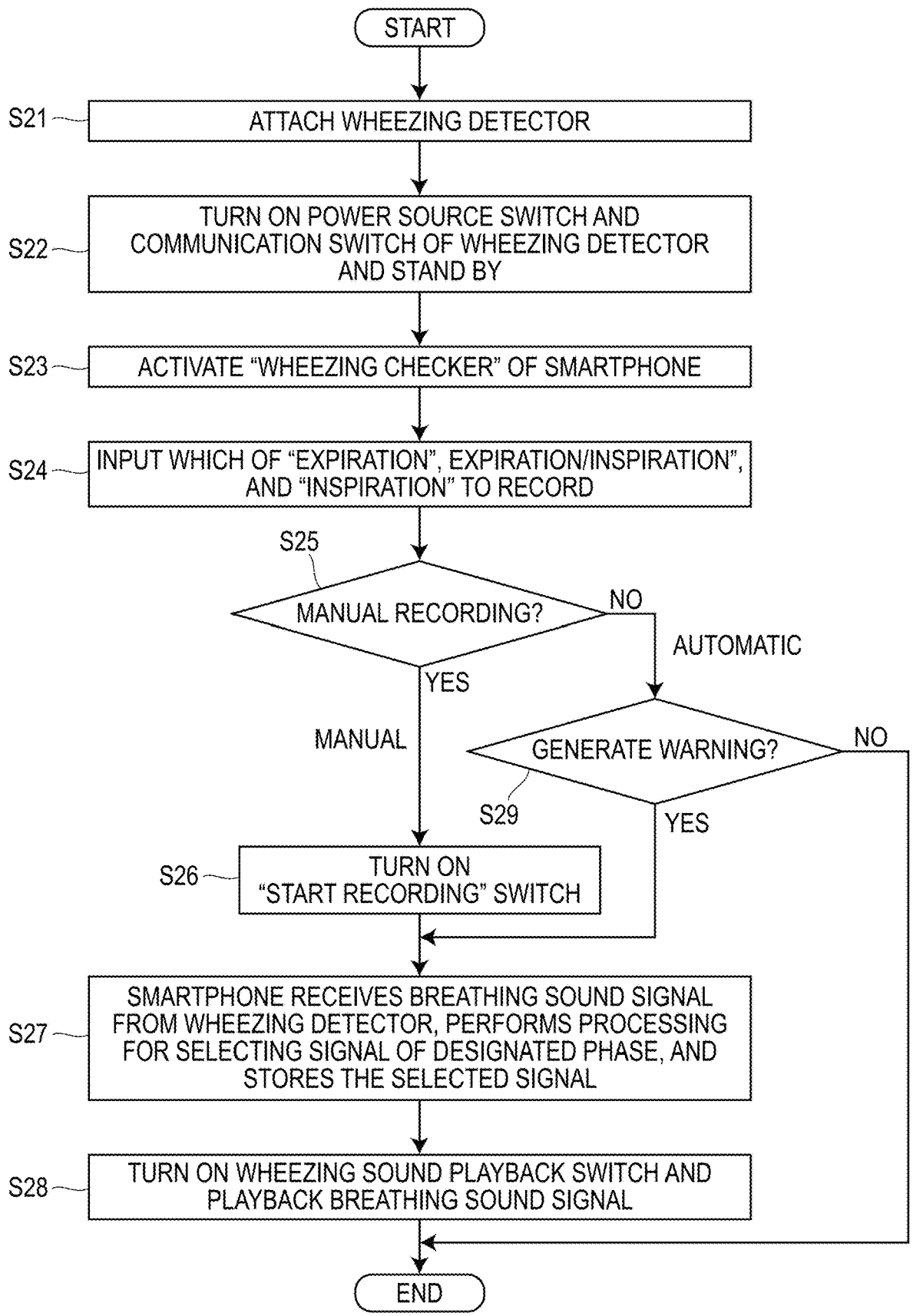
FIG. 19 is a flowchart showing a procedure of operations performed by a user in the case of recording and playing back the breathing sound using the smartphone.

FIG. 19 shows a procedure of operations according to which the user 91 records the breathing sound of the infant 90 in the memory 220 of the smartphone 200 using the wheezing detection system 1.

(1) Steps S21 to S23 in FIG. 19 advance similarly to steps S1 to S3 in FIG. 17. Here, in step S23 of FIG. 19, the initialization menu screen shown in FIG. 15(A) is displayed on the display screen 10 of the smartphone 200. A phase selection switch 40 serving as a phase instruction input unit is included on the initialization menu screen. When the breathing sound signal BS is to be recorded, the phase selection switch 40 includes an "expiration" switch 41 for selecting only the expiratory phase, an "expiration/inspiration" switch 42 for selecting both the expiratory phase and the inspiratory phase, and an "inspiration" switch 43 for selecting the inspiratory phase.

(2) In a state in which the phase selection switch 40 is displayed on the display screen 10 of the smartphone 200, according to a request made by the doctor, for example, the user 91 presses one switch among the "expiration" switch 41, the "expiration/inspiration" switch 42, and the "inspiration" switch 43 according to which of only the expiratory phase, both the expiratory phase and the inspiratory phase, and only the inspiratory phase is to be recorded (step S24 in FIG. 19). Accordingly, the phase to be recorded is selected.

(3) Next, the user 91 determines whether to manually record or automatically record (step S25 in FIG. 19). For example, if the current wheezing symptoms of the infant 90 are severe and the user 91 wants to record the wheezing immediately, it is desirable to select manual recording. On the other hand, if the current wheezing symptoms of the infant 90 are favorable and the user 91 wants to record when the wheezing symptoms become severe, it is desirable to select automatic recording.

(4) In the case of performing manual recording (YES in step S25 of FIG. 19), the user 91 presses the "start recording" switch 25 on the initialization menu screen shown in FIG. 15(A) (step S26 of FIG. 19). Upon doing so, the control unit 210 of the smartphone 200 instructs the wheezing detector 100 to transmit the breathing sound signal BS via the near field wireless communication unit 280. On the other hand, in the case of performing automatic recording, the user 91 uses the "setting" switch 22 shown in FIG. 15(A) to set that "automatic recording" is to be performed. In the "automatic recording" mode, the control unit 210 of the smartphone 200 waits for the above-described alarm signal (indicates that the percentage of the time for which the addition unit period reaches red R has exceeded the threshold β) from the wheezing detector 100 (step S29 in FIG. 19), and instructs the wheezing detector 100 to transmit the breathing sound signal BS via the near field wireless communication unit 280 at the time of receiving the alarm signal (YES in step S29 of FIG. 19). In both the case of manual recording and the case of automatic recording, when the wheezing detector 100 receives the instruction to transmit the breathing sound signal BS from the smartphone 200, the wheezing detector 100 transmits the breathing sound signal BS to the smartphone 200 via the near field wireless communication unit 180 (in particular, BT communication).

(5) Upon receiving the breathing sound signal BS, in the smartphone 200, the control unit 210 functions as a sound recording unit and performs recording by storing the phase of the breathing sound signal BS selected with the phase selection switch 40 in the memory 220 (step S27 in FIG. 19). More specifically, the control unit 210 of the smartphone 200 functions as the phase identification unit and detects the phases of the breathing sound signal BS as follows.

First, as shown in FIG. 6, the breathing sound signal BS has local minimums in synchronization with zero-crossing points at which the breathing flow amount signal BF transitions from negative (inspiration) to positive (expiration). Accordingly, the control unit 210 can obtain a breathing cycle tc of the measurement subject (in this example, the infant 90) by detecting the local minimums BS0, BS1, ... of the breathing sound signal BS.

Figure 13:
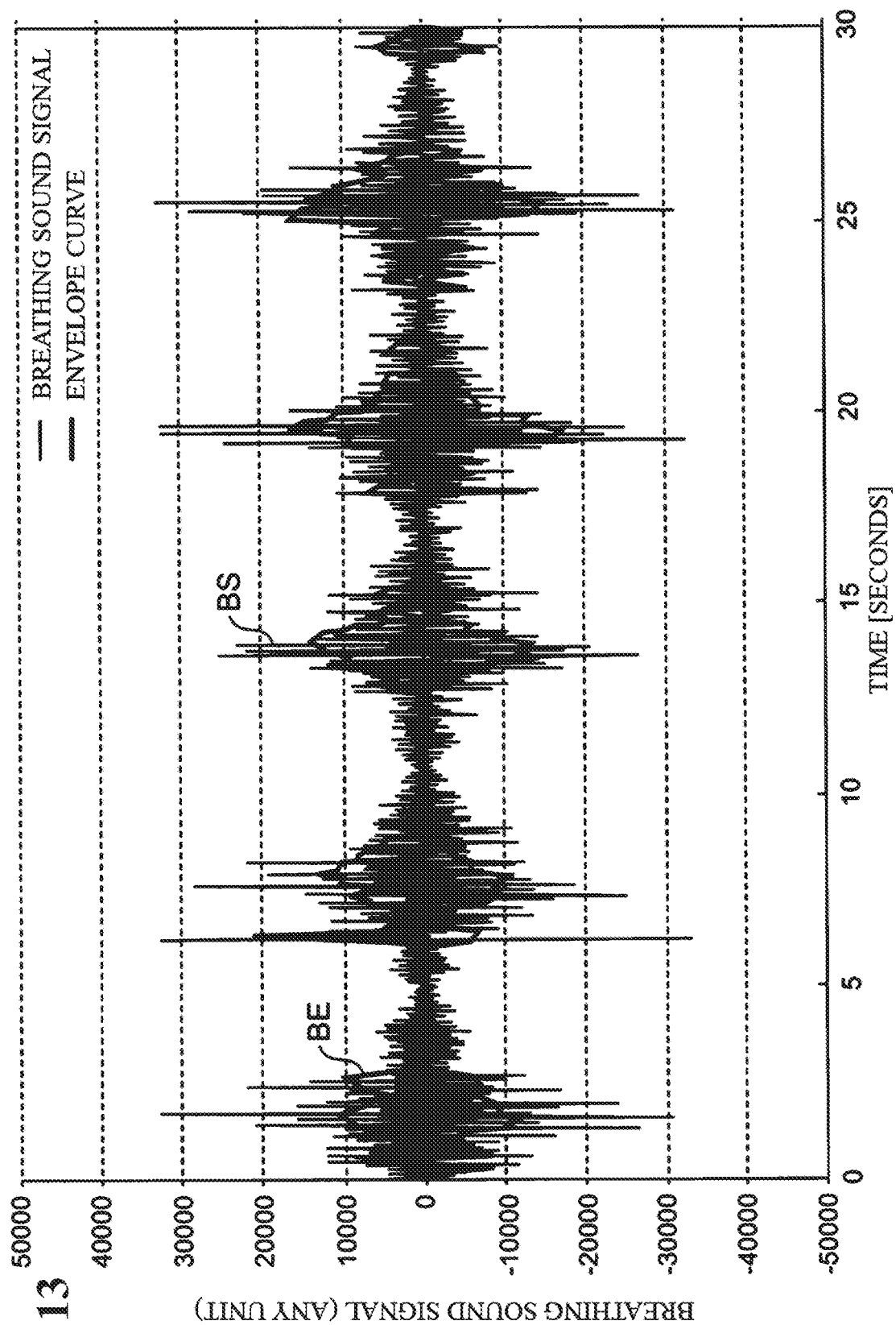
FIG. 13 is a diagram showing both a breathing sound signal detected by a microphone of the wheezing detector and an envelope curve calculated for the breathing sound signal.
Figure 14:
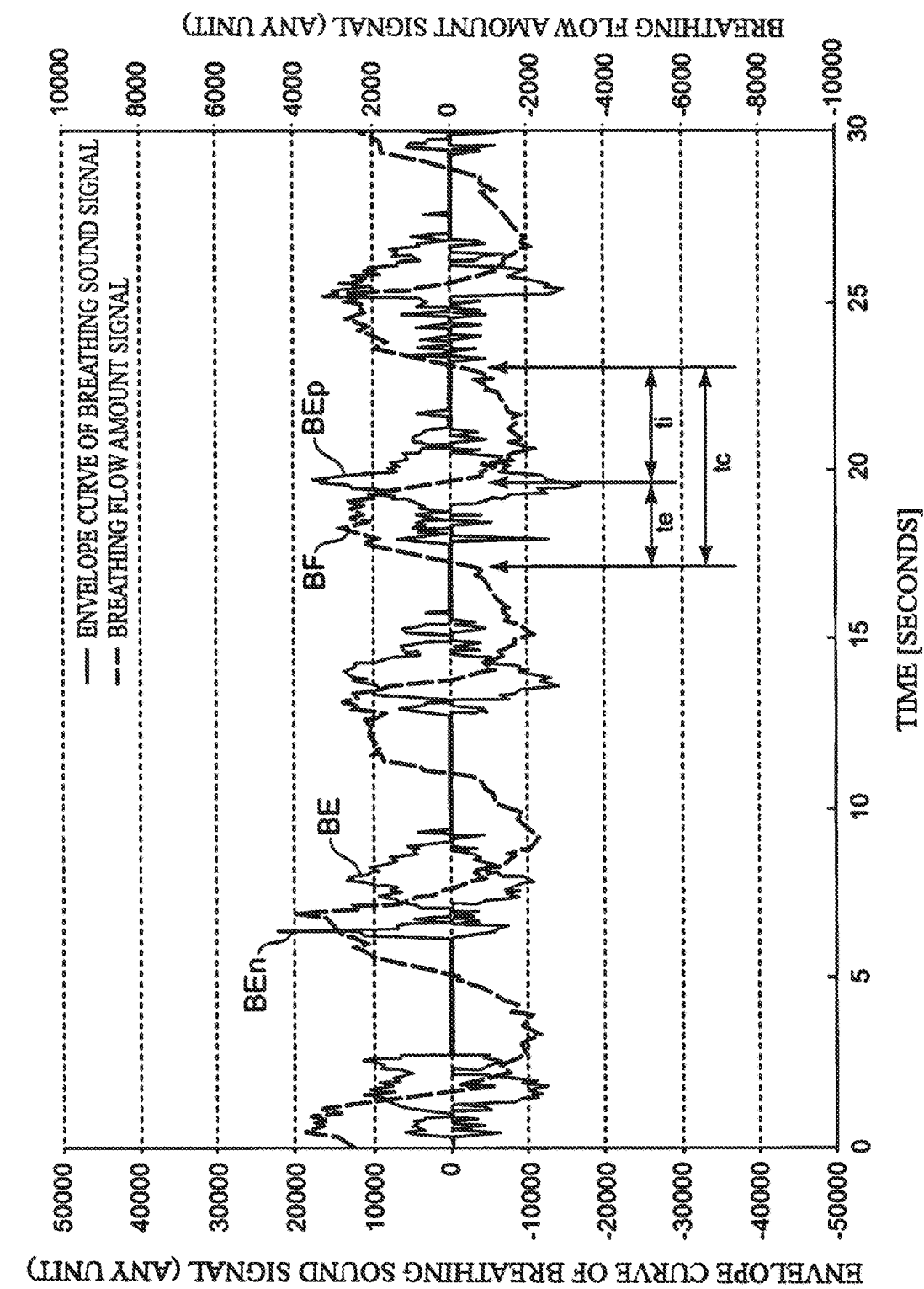
FIG. 14 is a diagram showing both the envelope curve shown in FIG. 13 and the breathing flow amount signal shown in FIG. 6.

Next, as shown in FIG. 13, the control unit 210 creates an envelope curve BE for the breathing sound signal BS (in this example, if the breathing sound signal BS is 3000 or less, it is replaced with 0 for the sake of ease). If the envelope BE for the breathing sound signal BS and the breathing flow amount signal BF shown in FIG. 6 are combined, as shown in FIG. 14, peaks BEp of the envelope curve BE are synchronous with the zero-crossing points at which the breathing flow amount signal BF transitions from positive (inspiration) to negative (expiration). Accordingly, the control unit 210 can distinguish between and identify the expiratory phase te and the inspiratory phase ti in the breathing cycle tc by detecting the peaks BEp of the envelope curve BE. Note that a peak BEn that is misaligned from the cycle of an original peak BEp in the envelope curve BE is ignored as noise based on the average cycle of the original peaks BEp.

Accordingly, upon distinguishing between and identifying the expiratory phase te and the inspiratory phase ti in the breathing cycle tc, the control unit 210 performs recording by storing the phase of the breathing sound signal BS selected using the phase selection switch 40 in the memory 220. Note that the "expiration" display 44 shown in FIG. 16(B) indicates that the expiration phase has been recorded.

Note that in the case of manual recording, when the user 91 presses the "stop recording" switch 26 on the initial menu screen shown in FIG. 15(A), recording performed by the smartphone 200 stops. The wheezing detector 100 receives a signal indicating "stop recording" via the near field wireless communication unit 180 and stops transmission of the breathing sound signal BS. In the automatic recording mode, the period in which the wheezing detector 100 transmits the breathing sound signal BS and the period in which the smartphone 200 performs recording are set to be 30 seconds starting from the recording start time by default (this can be changed and set by the user 91).

In the automatic recording mode, when the wheezing of the infant 90 serving as the measurement subject is relatively large (i.e., when the wheezing is severe), the breathing sound of the infant 90 can be automatically recorded. Accordingly, by replaying the recorded content the next time the infant 90 has a medical examination for example, the user 91 can have a doctor listen to the breathing sound of the infant 90 for when wheezing is severe. As a result, the doctor can more easily diagnose whether or not the infant 90 has asthma and the severity of the asthma, and can easily create a treatment plan. Note that if the smartphone 200 does not receive the alarm signal from the wheezing detector 100 (NO in step S29 of FIG. 19), recording will not be performed.

(6) Thereafter, by pressing the "wheezing sound playback" switch 64 on the screen shown in FIG. 12 for example, the user 91 can play back the breathing sound signal BS stored in the memory 220 with the speaker 260 for example (step S28 in FIG. 19).

According to this operation example, the phase of the breathing sound signal BS selected using the phase selection switch 40 can be recorded. Accordingly, if the phase requested by the doctor during the previous medical examination is selected, for example, the user 91 can have the doctor listen to the recorded content of the phase requested by the doctor among the breathing cycle tc when the user 91 has the doctor listen to the recorded content of the wheezing of the infant 90 during the next medical examination.

Also, the wheezing detection result (the bar graph AT shown in FIGS. 12 and 16(B)) displayed on the display screen 10 of the smartphone 200 and the recorded content of the breathing sound signal BS may be transmitted to a doctor's computer (a terminal in a hospital) via the network communication unit 290. Accordingly, the user 91 can receive a doctor's diagnosis at a remote location located away from the hospital.

In the above-described embodiment, the wheezing detection apparatus of the present invention is constituted as a wheezing detection system including the wheezing detector 100 and the smartphone 200, but there is no limitation to this. For example, instead of the smartphone 200, it is possible to include a commercially-available computer (a personal computer, etc.). In this case, the above-described "wheezing checker" program is installed in the commercially-available computer.

Also, the wheezing detection apparatus of the present invention may be constituted by only the smartphone 200, for example. In this case, the first microphone 111 and the second microphone 112 are connected to the smartphone 200, and the sound signal processing circuit 115 is mounted in the smartphone 200 (the function of the sound signal processing circuit 115 may be constituted by software and may be executed by the control unit 210). In this case, the wheezing detection apparatus of the present invention can be made small and compact. This configuration is advantageous in the case where the measurement subject is the user of the smartphone 200.

In the above-described embodiment, the temporal change in the frequency of wheezing was displayed as a bar graph AT, but there is no limitation to this. The temporal change in the frequency of wheezing may be displayed as another form of graph. For example, the temporal change in only the percentage (%) of time obtained by combining yellow Y and red R may be displayed as a bar graph.

The above-described embodiment is merely an example, and various modifications are possible without departing from the scope of the invention. The multiple above-described embodiments can be realized independently, but it is also possible to combine embodiments. Also, the various characteristics of the different embodiments can be realized independently, but it is also possible to combine characteristics of different embodiments.

REFERENCE SIGNS LIST

1 Wheezing detection system
10 Display screen
50 Wheezing detection result display field
100 Wheezing detector
111 First microphone
112 Second microphone
200 Smartphone
AT Bar graph
AT1, AT2, AT3, AT4 Bar
T1, T2, T3, T4 Addition unit period
Tw1, Tw2, Tw3, Tw4 Wheezing period

The invention claimed is:

1. A wheezing detection system, comprising:
a breathing sound detection unit configured to detect a breathing sound of a measurement subject and acquire a breathing sound signal in a time series expressing the breathing sound;
a processor configured to:
set a plurality of addition unit periods,
set a plurality of pre-determined processing unit periods within each of the plurality of addition unit periods,
in each of the plurality of pre-determined processing unit periods, convert the breathing sound signal into a frequency space to acquire a frequency spectrum of the breathing sound,
select a dominant peak having the largest area among a plurality of peaks in the frequency spectrum in each pre-determined processing unit period;
determine whether or not the dominant peak indicates wheezing based on a parameter (L/D) calculated from a height and a width of the peak,
collect the dominant peaks indicated as wheezing in each addition unit period, and
classify the collected dominant peaks into different levels to represent different powers of wheezing; and
a display configured to display an amount of dominant peaks in the different levels in each addition unit period.

2. The wheezing detection system according to claim 1, wherein
the processor determines whether or not the wheezing is indicated based on only the dominant peak having the largest area among the plurality of peaks in the frequency spectrum in a graph of frequency with respect to sound pressure.

3. The wheezing detection system according to claim 1, wherein
the processor determines that the wheezing is indicated only if the peak has a frequency ranging from 200 Hz to 1500 Hz in the frequency spectrum.

4. The wheezing detection system according to claim 2, wherein
the processor is further configured to:
add up the lengths of the processing unit periods that were determined to include the wheezing in each of the plurality of addition unit periods, and obtain the result as a wheezing period,
add up the lengths of the processing unit periods that were determined to include the wheezing in each of the different levels; and
generate a warning when a percentage of time for one of the different levels in one of the addition unit periods exceeds a pre-determined second threshold value based on the addition performed by the processor.

5. The wheezing detection system according to claim 4, comprising
a sound recording unit configured to record the breathing sound signal when the processor generates the warning.

6. The wheezing detection system according to claim 1, further comprising:
a phase identification unit configured to identify a breathing cycle of the measurement subject and divide the breathing cycle into an expiratory phase and an inspiratory phase, based on the breathing sound signal acquired by the breathing sound detection unit;

a phase instruction input unit configured to input an instruction to select one or both of the expiratory phase and the inspiratory phase of the breathing sound signal; and a sound recording unit configured to record the one or both of the expiratory phase and the inspiratory phase of the breathing sound signal instructed by the phase instruction input unit.

7. The wheezing detection system according to claim 1, wherein the breathing sound detection unit includes:

a first microphone in the form of a stethoscope attachable to skin of the chest of the measurement subject; and a second microphone attachable to clothing or skin of a part located away from the chest and respiratory organ of the measurement subject, and the breathing sound detection unit outputs a difference obtained by subtracting the output of the second microphone from the output of the first microphone.

* * * * *